(12) United States Patent
Yakushiji et al.

(10) Patent No.: US 10,825,995 B2
(45) Date of Patent: Nov. 3, 2020

(54) MATERIAL FOR PHOTOELECTRIC CONVERSION ELEMENT FOR AN IMAGING ELEMENT, AND PHOTOELECTRIC CONVERSION ELEMENT INCLUDING SAME

(71) Applicant: NIPPON KAYAKU KABUSHIKI KAISHA, Tokyo (JP)

(72) Inventors: Hidenori Yakushiji, Tokyo (JP); Kazuki Niimi, Saitama (JP); Ryoutarou Morita, Saitama (JP); Tatsuya Yamamoto, Tokyo (JP); Toshifumi Inouchi, Tokyo (JP); Masahiro Hamada, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/052,303

(22) Filed: Aug. 1, 2018

(65) Prior Publication Data
US 2018/0375033 A1 Dec. 27, 2018

Related U.S. Application Data

(62) Division of application No. 15/304,628, filed as application No. PCT/JP2015/062201 on Apr. 22, 2015, now abandoned.

(30) Foreign Application Priority Data

Apr. 25, 2014 (JP) .................................. 2014-091410
Feb. 16, 2015 (JP) .................................. 2015-027179

(51) Int. Cl.
C07D 495/04 (2006.01)
H01L 51/00 (2006.01)
(Continued)

(52) U.S. Cl.
CPC ........ *H01L 51/0074* (2013.01); *C07D 495/04* (2013.01); *H01L 27/146* (2013.01);
(Continued)

(58) Field of Classification Search
CPC . H01L 51/0024; H01L 51/424; H01L 51/441; H01L 31/10; H01L 27/146;
(Continued)

(56) References Cited

U.S. PATENT DOCUMENTS 9,260,451 B2    2/2016  Takimiya
2006/0044561 A1    3/2006  Kazumi
(Continued)

FOREIGN PATENT DOCUMENTS

JP    2006-339424 A    12/2006
JP    2008-290963 A    12/2008
(Continued)

OTHER PUBLICATIONS

Kazuo Takimiya et al., "2,7-Diphenyl[1]benzothieno[3,2-b]benzothiophene, A New Organic Semiconductor for Air-Stable Organic Field-Effect Transistors with Mobilities up to 2.0 cm2 V-1 s-1", J. Am. Chem. Soc., 2006, 128, pp. 12604-12605.
(Continued)

*Primary Examiner* — Taylor V Oh
(74) *Attorney, Agent, or Firm* — Greenblum & Bernstein, P.L.C.

(57) ABSTRACT

The present invention provides a material for photoelectric conversion elements for use in imaging elements which comprises a compound represented by the following formula (1). The material for photoelectric conversion elements for use in imaging elements, which comprises a compound represented by the following formula (1), is used to produce a photoelectric conversion element which is excellent in
(Continued)

terms of hole- or electron-leakage prevention, thermal resistance to processing temperatures, transparency to visible light, etc. In formula (1), $R_1$ and $R_2$ each independently represent a substituted or unsubstituted aromatic group.

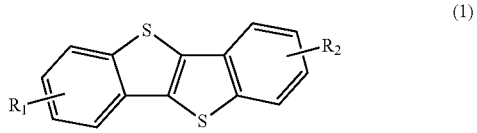

(1)

21 Claims, 1 Drawing Sheet

(51) Int. Cl.
    *H01L 27/146*      (2006.01)
    *H01L 51/42*      (2006.01)
    *H01L 31/10*      (2006.01)
    *H01L 27/30*      (2006.01)
    *H01L 51/44*      (2006.01)

(52) U.S. Cl.
    CPC ............ *H01L 31/10* (2013.01); *H01L 51/424* (2013.01); *H01L 27/307* (2013.01); *H01L 51/441* (2013.01); *H01L 2251/308* (2013.01); *Y02E 10/549* (2013.01)

(58) Field of Classification Search
    CPC ............ H01L 2251/308; H01L 27/307; C07D 495/04; Y02E 10/549

USPC .......................................................... 549/42
See application file for complete search history.

(56) References Cited

U.S. PATENT DOCUMENTS

| | | |
|---|---|---|
| 2006/0278869 A1 | 12/2006 | Hioki et al. |
| 2009/0001357 A1 | 1/2009 | Takimiya |
| 2010/0308311 A1 | 12/2010 | Mitsui et al. |
| 2011/0108813 A1 | 5/2011 | Kohiro |

FOREIGN PATENT DOCUMENTS

| | | | |
|---|---|---|---|
| JP | 2009-021390 A | 1/2009 |
| JP | 2009-152355 A | 7/2009 |
| JP | 2009-267372 A | 11/2009 |
| JP | 2010-232413 A | 10/2010 |
| JP | 2011-176259 A | 9/2011 |
| JP | 2012-119502 A | 6/2012 |
| JP | 4945146 B2 | 6/2012 |
| JP | 4972288 B2 | 7/2012 |
| JP | 5022573 B2 | 9/2012 |
| WO | 2006/077888 A1 | 7/2006 |
| WO | 2009/122956 A1 | 10/2009 |
| WO | 2009/128559 A | 10/2009 |

OTHER PUBLICATIONS

International Search Report issued with respect to Application No. PCT/JP2015/062201, dated Jul. 21, 2015.
International Preliminary Report on Patentability issued with respect to Application No. PCT/JP2015/062201, dated Oct. 25, 2016.
Office Action in TW Patent App. No. 108110092 dated Mar. 31, 2020.

[Figure 1]
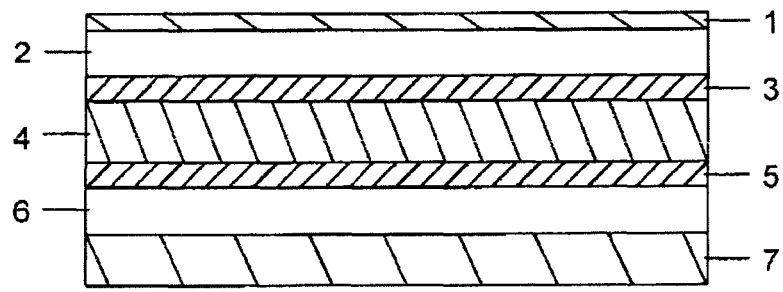
[Figure 2]
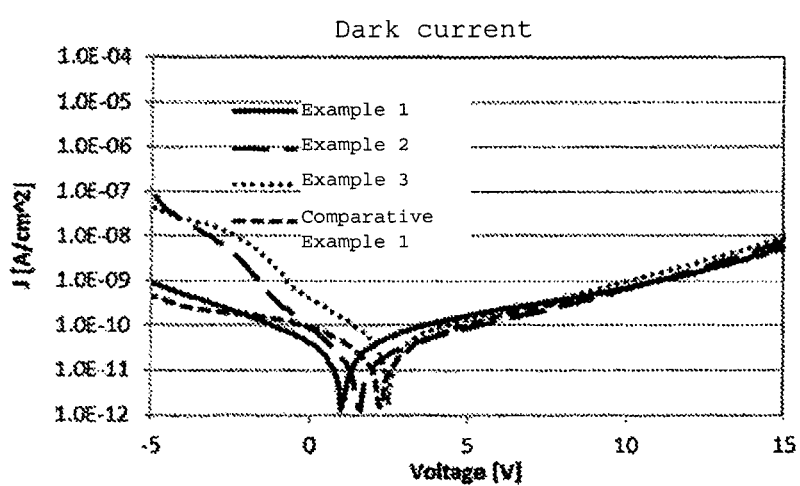
[Figure 3]
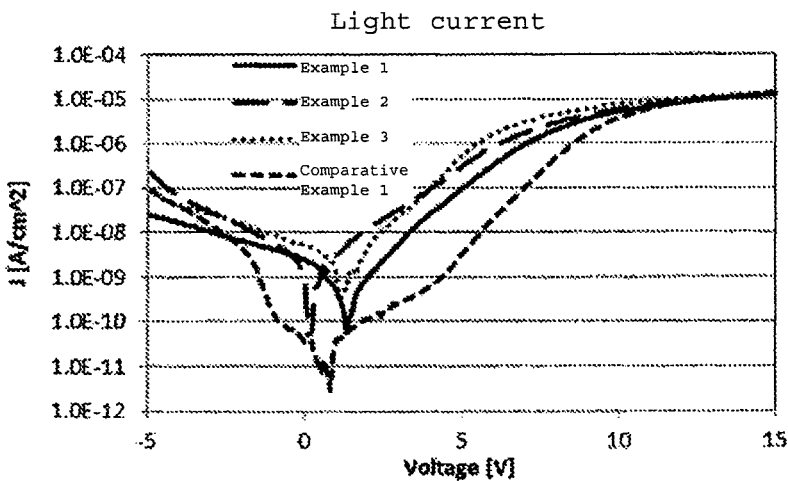

MATERIAL FOR PHOTOELECTRIC CONVERSION ELEMENT FOR AN IMAGING ELEMENT, AND PHOTOELECTRIC CONVERSION ELEMENT INCLUDING SAME

The present application is a Divisional Application of U.S. application Ser. No. 15/304,628, filed on Oct. 17, 2016, which is a National Stage of International Patent Application No. PCT/JP2015/062201, filed on Apr. 22, 2015, which claims priority to Japanese Application No. 2014-091410, filed on Apr. 25, 2014, and Japanese Application No. 2015-027179, filed on Feb. 16, 2015. The disclosures of U.S. application Ser. No. 15/304,628 and International Patent Application No. PCT/JP2015/062201 are incorporated by reference herein in their entireties.

TECHNICAL FIELD

The present invention relates to a photoelectric conversion element, an imaging element, a photosensor, and a material for a photoelectric conversion element for use in an imaging element which is used for these devices.

BACKGROUND ART

In recent years, organic electronic devices have received growing attention. Examples of their features include flexible structures, possible large areas, and inexpensive and high-speed printing methods available in electronic device manufacturing processes. Typical examples of the devices include organic EL elements, organic solar cell elements, organic photoelectric conversion elements, and organic transistor elements. The organic EL elements are expected as main targets for next-generation display purposes as flat panel displays and applied to mobile phone displays, TV, etc. The organic EL elements are still under development with the aim of higher functionalization. Research and development are ongoing as to the organic solar cell elements, etc., as flexible and inexpensive energy sources, and the organic transistor elements, etc., as flexible displays or inexpensive IC.

For the development of the organic electronic devices, it is very important to develop materials constituting the devices. Therefore, a large number of materials have been studied in each field. Nonetheless, such materials do not have sufficient performance, and materials useful for various devices are still being developed energetically. Among others, compounds having a benzothienobenzothiophene backbone have been developed as organic electronic materials. Among these compounds, a compound having a phenylbenzothienobenzothiophene backbone has also been reported as an organic transistor (Non Patent Literature 1 and Patent Literature 1) and has been reported to be applied to, particularly, a vertical transistor element (Patent Literature 2).

Meanwhile, in recent organic electronics, the organic photoelectric conversion elements are expected to be expanded to next-generation imaging elements, and some groups have made reports thereon. Examples of such cases include use of a quinacridone derivative or a quinazoline derivative in a photoelectric conversion element (Patent Literature 3), application of a photoelectric conversion element containing a quinacridone derivative to an imaging element (Patent Literature 4), and use of a diketopyrrolopyrrole derivative (Patent Literature 5) In general, it is considered that the performance of imaging elements is improved by intended reduction in dark current for the purpose of high contrasts and electric power saving. Thus, an approach of inserting a hole blocking layer or an electron blocking layer to between a photoelectric conversion portion and an electrode portion is used for decreasing leakage current from the photoelectric conversion portion in the dark.

The hole blocking layer and the electron blocking layer are generally used widely in the field of organic electronic devices. In films constituting a device, each of the hole blocking layer and the electron blocking layer is disposed at the interface between an electrode or a conductive film and the other films, and has the function of controlling the back transfer of holes or electrons. The hole blocking layer or the electron blocking layer adjusts the leakage of unnecessary holes or electrons and is selected for use in consideration of characteristics such as thermal resistance, transmitted wavelengths, and film formation methods depending on the purpose of the device. However, the required performance of materials, particularly, for photoelectric conversion element purposes, is high, and existing hole blocking layers or electron blocking layers do not have sufficient performance in terms of leakage current prevention properties, thermal resistance to processing temperatures, transparency to visible light, etc., and are in short of commercial exploitation.

CITATION LIST

Patent Literature

Patent Literature 1: International Publication No. WO 2006/077888
Patent Literature 2: Japanese Patent Laid-Open No. 2010-232413
Patent Literature 3: Japanese Patent No. 4972288
Patent Literature 4: Japanese Patent No. 4945146
Patent Literature 5: Japanese Patent No. 5022573
Patent Literature 6: Japanese Patent Laid-Open No. 2008-290963

Non Patent Literature

Non Patent Literature 1: J. Am. Chem. Soc., 2006, 128 (39), 12604

SUMMARY OF INVENTION

Technical Problem

The present invention has been made in light of these circumstances, and an object of the present invention is to provide various electronic devices including a photoelectric conversion element which are excellent in hole- or electron-leak prevention properties, hole or electron transport properties, thermal resistance to processing temperatures, transparency to visible light, etc.

Solution to Problem

The present inventors has conducted diligent studies to attain the object and consequently completed the present invention by finding that the object is attained by applying a compound represented by the formula (1) given below to a photoelectric conversion element.

Specifically, the present invention is as follows:
[1] a material for a photoelectric conversion element for use in an imaging element, comprising a compound represented by the following formula (1):

[Formula 1]

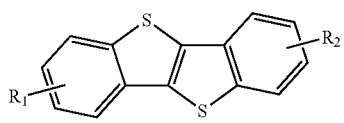

(1)

wherein $R_1$ and $R_2$ each independently represent a substituted or unsubstituted aromatic group;
[2] the material for a photoelectric conversion element for use in an imaging element according to [1], wherein the compound of the formula (1) is a compound represented by the following formula (2):

[Formula 2]

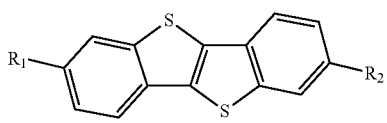

(2)

wherein $R_1$ and $R_2$ are as defined in the formula (1) according to [1];
[3] the material for a photoelectric conversion element for use in an imaging element according to [1] or [2], wherein $R_1$ and $R_2$ in the formula (1) or the formula (2) are each independently a substituted or unsubstituted aromatic hydrocarbon group;
[4] the material for a photoelectric conversion element for use in an imaging element according to [3], wherein each of $R_1$ and $R_2$ in the formula (1) or the formula (2) is a substituted or unsubstituted phenyl group;
[5] the material for a photoelectric conversion element for use in an imaging element according to [4], wherein each of $R_1$ and $R_2$ in the formula (1) or the formula (2) is a phenyl group having a substituted or unsubstituted aromatic hydrocarbon group;
[6] the material for a photoelectric conversion element for use in an imaging element according to [5], wherein each of $R_1$ and $R_2$ in the formula (1) or the formula (2) is a phenyl group having a substituted or unsubstituted phenyl group;
[7] the material for a photoelectric conversion element for use in an imaging element according to [6], wherein each of $R_1$ and $R_2$ in the formula (1) or the formula (2) is a phenyl group having a biphenyl group;
[8] the material for a photoelectric conversion element for use in an imaging element according to [4], wherein each of $R_1$ and $R_2$ in the formula (1) or the formula (2) is a phenyl group having an alkyl group having 1 to 12 carbon atoms;
[9] the material for a photoelectric conversion element for use in an imaging element according to [8], wherein each of $R_1$ and $R_2$ in the formula (1) or the formula (2) is a phenyl group having a methyl group or an ethyl group;
[10] a photoelectric conversion element for use in an imaging element, comprising a material for a photoelectric conversion element for use in an imaging element according to any one of [1] to [9];
[11] a photoelectric conversion element for use in an imaging element, the photoelectric conversion element having (A) a first electrode film, (B) a second electrode film, and (C) a photoelectric conversion portion disposed between the first electrode film and the second electrode film, wherein the photoelectric conversion portion (C) comprises at least (c-1) a photoelectric conversion layer and (c-2) an organic thin-film layer other than the photoelectric conversion layer, and the organic thin-film layer (c-2) other than the photoelectric conversion layer comprises a material for a photoelectric conversion element for use in an imaging element according to any one of [1] to [9];
[12] the photoelectric conversion element for use in an imaging element according to [11], wherein the organic thin-film layer (c-2) other than the photoelectric conversion layer is an electron blocking layer;
[13] the photoelectric conversion element for use in an imaging element according to [11], wherein the organic thin-film layer (c-2) other than the photoelectric conversion layer is a hole blocking layer;
[14] the photoelectric conversion element for use in an imaging element according to [11], wherein the organic thin-film layer (c-2) other than the photoelectric conversion layer is an electron transport layer;
[15] the photoelectric conversion element for use in an imaging element according to [11], wherein the organic thin-film layer (c-2) other than the photoelectric conversion layer is a hole transport layer;
[16] the photoelectric conversion element for use in an imaging element according to any one of [10] to [15], further having (D) a thin-film transistor having a hole accumulation portion and (E) a signal readout portion which reads a signal responding to charge accumulated in the thin-film transistor;
[17] the photoelectric conversion element for use in an imaging element according to [16], wherein the thin-film transistor (D) having a hole accumulation portion further has (d) a connection portion which electrically connects the hole accumulation portion to any one of the first electrode film and the second electrode film;
[18] an imaging element in which a plurality of photoelectric conversion elements for use in an imaging element according to any one of [10] to [17] are arranged in an array pattern; and
[19] a photosensor comprising a photoelectric conversion element for use in an imaging element according to any one of [10] to [17] or an imaging element according to [18].

Advantageous Effects of Invention

The present invention can provide a novel photoelectric conversion element for use in an imaging element which comprises a compound represented by the formula (1) and is excellent in required characteristics such as hole- or electron-leakage prevention, hole or electron transport properties, thermal resistance, and transparency to visible light.

BRIEF DESCRIPTION OF DRAWINGS

FIG. 1 shows a cross-sectional view illustrating an embodiment of the photoelectric conversion element for use in an imaging element of the present invention.

FIG. 2 shows a dark current-voltage graph of photoelectric conversion elements for use in an imaging element in Example 1, Example 2, Example 3, and Comparative Example 1.

FIG. 3 shows a light current-voltage graph of the photoelectric conversion elements for use in an imaging element in Example 1, Example 2, Example 3, and Comparative Example 1.

DESCRIPTION OF EMBODIMENTS

The contents of the present invention will be described in detail. The explanation about configuration requirements described below is based on typical embodiments and specific examples of the present invention. However, the present invention is not intended to be limited by such embodiments or specific examples.

The material for a photoelectric conversion element for use in an imaging element of the present invention comprises a compound represented by the following general formula (1):

[Formula 3]

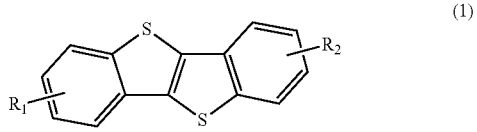

(1)

In the formula (1), $R_1$ and $R_2$ each independently represent a substituted or unsubstituted aromatic group. In this context, the "substituted or unsubstituted aromatic group" means an aromatic group having at least one substituent or an aromatic group having no substituent. When the aromatic group has substituent(s), the aromatic group can have at least one substituent, and the position of substitution and the number of substituents are not particularly limited.

Specific examples of the aromatic group represented by each of $R_3$ and $R_2$ in the formula (1) include: aromatic hydrocarbon groups such as a phenyl group, a biphenyl group, a naphthyl group, an anthryl group, a phenanthryl group, a pyrenyl group, and a benzopyrenyl group; heterocyclic groups such as a pyridyl group, a pyrazyl group, a pyrimidyl group, a quinolyl group, an isoquinolyl group, a pyrrolyl group, an indolenyl group, an imidazolyl group, a carbazolyl group, a thienyl group, a furyl group, a pyranyl group, and a pyridonyl group; and condensed heterocyclic groups such as a benzoquinolyl group, an anthraquinolyl group, and a benzothienyl group. Among these, an aromatic hydrocarbon group or a heterocyclic group is preferred. The aromatic group is more preferably a phenyl group, a biphenyl group, a naphthyl group, a phenanthryl group, or a carbazolyl group, further preferably a phenyl group, a phenanthryl group, or a carbazolyl group, particularly preferably a phenyl group or a biphenyl group. Also preferably, both of $R_1$ and $R_2$ are the same groups.

Examples of the substituent on the aromatic group represented by each of $R_1$ and $R_2$ in the formula (I) include, but are not limited to, an alkyl group, an alkoxy group, an aromatic group, a halogen atom, a hydroxyl group, a mercapto group, a nitro group, an alkyl-substituted amino group, an aryl-substituted amino group, an unsubstituted amino group ($NH_2$ group), an acyl group, an alkoxycarbonyl group, a cyano group, and an isocyano group.

Specific examples of the alkyl group as the substituent on the aromatic group represented by each of $R_1$ and $R_2$ in the formula (1) include alkyl groups each having 1 to 36 carbon atoms, such as a methyl group, an ethyl group, a propyl group, an iso-propyl group, a n-butyl group, an iso-butyl group, a t-butyl group, a n-pentyl group, an iso-pentyl group, a t-pentyl group, a sec-pentyl group, a n-hexyl group, an iso-hexyl group, a n-heptyl group, a sec-heptyl group, a n-octyl group, a n-nonyl group, a sec-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosyl group, a docosyl group, a n-pentacosyl group, a n-octacosyl group, a n-tricontyl group, a 5-(n-pentyl)decyl group, a heneicosyl group, a tricosyl group, a tetracosyl group, a hexacosyl group, a heptacosyl group, a nonacosyl group, a n-triacontyl group, a squaryl group, a dotriacontyi group, and hexatriacontyi group. The alkyl group is preferably an alkyl group having 1 to 24 carbon atoms, more preferably an alkyl group having 1 to 20 carbon atoms, further preferably an alkyl group having 1 to 12 carbon atoms, particularly preferably an alkyl group having 1 to 6 carbon atoms, most preferably an alkyl group having 1 to 4 carbon atoms.

Specific examples of the alkoxy group as the substituent on the aromatic group represented by each of $R_1$ and $R_2$ in the formula (1) include alkoxy groups each having 1 to 36 carbon atoms, such as a methoxy group, an ethoxy group, a propoxy group, an iso-propoxy group, a n-butoxy group, an iso-butoxy group, a t-butoxy group, a n-pentyloxy group, an iso-pentyloxy group, a t-pentyloxy group, a sec-pentyloxy group, a n-hexyloxy group, an iso-hexyloxy group, a n-heptyloxy group, a sec-heptyloxy group, a n-octyloxy group, a n-nonyloxy group, a sec-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group, a n-eicosyloxy group, a docosyloxy group, a n-pentacosyloxy group, a n-octacosyloxy group, a n-tricontyloxy group, a 5-(n-pentyl)decyloxy group, a heneicosyloxy group, a tricosyloxy group, a tetracosyloxy group, a hexacosyloxy group, a hieptacosylaoxy group, a nonacosyioxy group, a n-triacontyloxy group, a squaryloxy group, a dotriacontyloxy group, and a hexatriacontyloxy group. The alkoxy group is preferably an alkoxy group having 1 to 24 carbon atoms, more preferably an alkoxy group having 1 to 20 carbon atoms, further preferably an alkoxy group having 1 to 12 carbon atoms, particularly preferably an alkoxy group having 1 to 6 carbon atoms, most preferably an alkoxy group having 1 to 4 carbon atoms.

Specific examples of the aromatic group as the substituent on the aromatic group represented by each of $R_1$ and $R_2$ in the formula (1) include the same as those mentioned about the aromatic group represented by each of $R_1$ and $R_2$ in the formula (1). The preferred aromatic group is also the same as those mentioned about the aromatic group represented by each of $R_1$ and $R_2$ in the formula (1).

Specific examples of the halogen atom as the substituent on the aromatic group represented by each of $R_1$ and $R_2$ in the formula (1) include a fluorine atom, a chlorine atom, a bromine atom, and an iodine atom.

The alkyl-substituted amino group as the substituent on the aromatic group represented by each of $R_1$ and $R_2$ in the formula (1) is not limited to any of monoalkyl-substituted amino groups and dialkyl-substituted amino groups. Examples of the alkyl group for these alkyl-substituted amino groups include the same as those listed as the alkyl group as the substituent on the aromatic group represented by each of $R_1$ and $R_2$ in the formula (1).

The aryl-substituted amino group as the substituent on the aromatic group represented by each of $R_1$ and $R_2$ in the formula (1) is not limited to any of monoaryl-substituted amino groups and diaryl-substituted amino groups. Examples of the aryl group for these aryl-substituted amino groups include the same as the aromatic hydrocarbon groups described as the aromatic group represented by each of $R_1$ and $R_2$ in the formula (1).

Examples of the acyl group as the substituent on the aromatic group represented by each of $R_1$ and $R_2$ in the formula (1) include substituents composed of a carbonyl group (=CO group) bonded to the aromatic hydrocarbon group described as the aromatic group represented by each of $R_1$ and $R_2$ in the formula (1) or the alkyl group as the substituent on the aromatic group represented by each of $R_1$ and $R_2$ in the formula (1).

Examples of the alkoxycarbonyl group as the substituent on the aromatic group represented by each of $R_1$ and $R_2$ in the formula (1) include substituents composed of a carbonyl group bonded to the alkoxy group as the substituent on the aromatic group represented by each of $R_1$ and $R_2$ in the formula (1).

The substituent on the aromatic group represented by each of $R_1$ and $R_2$ in the formula (1) is preferably an alkyl group, an aromatic group, a halogen atom, or an alkoxyl group, more preferably an alkyl group or an aromatic hydrocarbon group, further preferably a methyl group, an ethyl group, or a phenyl group, particularly preferably a methyl group or an ethyl group.

Specifically, $R_1$ and $R_2$ in the formula (1) are each independently preferably an aromatic hydrocarbon group or a heterocyclic group optionally having substituent(s) selected from the group consisting of an alkyl group, an aromatic hydrocarbon group, a halogen atom, and an alkoxyl group, each independently more preferably a phenyl group, a naphthyl group, a phenanthryl group, or a carbazolyl group optionally having substituent(s) selected from the group consisting of an alkyl group and an aromatic hydrocarbon group, each independently particularly preferably a phenyl group, a phenanthryl group, or a carbazolyl group optionally having substituent(s) selected from the group consisting of a methyl group, an ethyl group, a phenyl group, and a biphenyl group, each independently most preferably a phenyl group optionally having substituent(s) selected from the group consisting of a methyl group, a phenyl group, and a biphenyl group. In these preferred forms, further preferably, $R_1$ and $R_2$ are the same groups.

More specifically, both of $R_1$ and $R_2$ in the formula (1) are preferably the same unsubstituted phenyl groups, the same phenyl groups having an alkyl group having 1 to 4 carbon atoms at the 4-position, the same phenyl groups having a phenyl group or a biphenyl group (the position of substitution by the phenyl group or the biphenyl group can be any of the 2-position, the 3-position, and the 4-position), the same phenyl groups having phenyl groups at the 3-position and the 5-position, the same unsubstituted phenanthryl groups, or the same unsubstituted carbazolyl group.

More specifically, both of $R_1$ and $R_2$ in the formula (1) are more preferably the same unsubstituted phenyl groups, the same phenyl groups having an alkyl group having 1 to 4 carbon atoms at the 4-position, the same phenyl groups having a phenyl group or a biphenyl group (the position of substitution by the phenyl group or the biphenyl group can be any of the 2-position, the 3-position, and the 4-position), or the same phenyl groups having phenyl groups at the 3-position and the 5-position.

More specifically, both of $R_1$ and $R_2$ in the formula (1) are further preferably the same phenyl groups having a phenyl group or a biphenyl group (the position of substitution by the phenyl group or the biphenyl group can be any of the 2-position, the 3-position, and the 4-position), or the same phenyl groups having phenyl groups at the 3-position and the 5-position.

More specifically, both of $R_1$ and $R_2$ in the formula (1) are particularly preferably the same phenyl groups having a phenyl group or a biphenyl group (the position of substitution by the phenyl group or the biphenyl group can be any of the 2-position, the 3-position, and the 4-position).

More specifically, both of $R_1$ and $R_2$ in the formula (1) are most preferably the same phenyl groups having a biphenyl group (the position of substitution by the biphenyl group can be any of the 2-position, the 3-position, and the 4-position).

The position of substitution on each of $R_1$ and $R_2$ in the formula (1) is not particularly limited and is preferably the 2,7-position in [1]benzothieno[3,2-b][1]benzothiophene in the formula (1). Specifically, the compound represented by the formula (1) is preferably a compound represented by the following general formula (2):

[Formula 4]

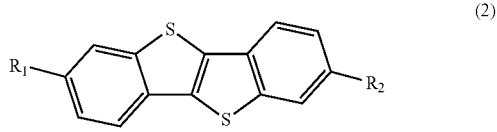

In the formula (2), $R_1$ and $R_2$ are as defined in the formula (1). Preferred $R_1$ and $R_2$ are also the same as in the formula (1).

Specifically, the compound represented by the formula (2) is preferably a compound of the formula (2) wherein both of $R_1$ and $R_2$ take the preferred to most preferred forms in the formula (1) described above, more preferably a compound represented by the formula (20), (21), (25), or (26) in specific examples mentioned later, even more preferably a compound represented by the formula (20) or (25) in the specific examples, further preferably a compound represented by the formula (25) in the specific examples.

The compound represented by the formula (1) can be synthesized by, for example, any of methods known in the art which are disclosed in Patent Literature 1, Patent Literature 6, and Non Patent Literature 1. Examples of such methods include a method described in Scheme 1 below. A nitrostilbene derivative (A) is used as a starting material, and the desired compound can be obtained by forming a benzothienobenzothiophene skeleton (D) and subsequently converting the resulting compound to an aminated form (E) and then to a halogenated form (F), followed by coupling with a boric acid derivative. The method of Patent Literature 5 is more effective because the desired compound can b manufactured in one step from the corresponding benzaldehyde derivative.

[Formula 5]

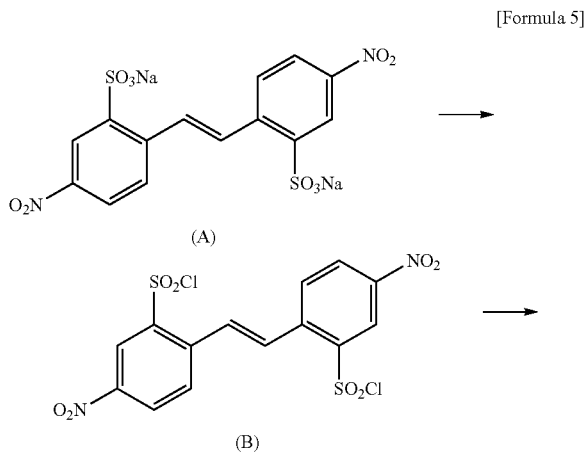

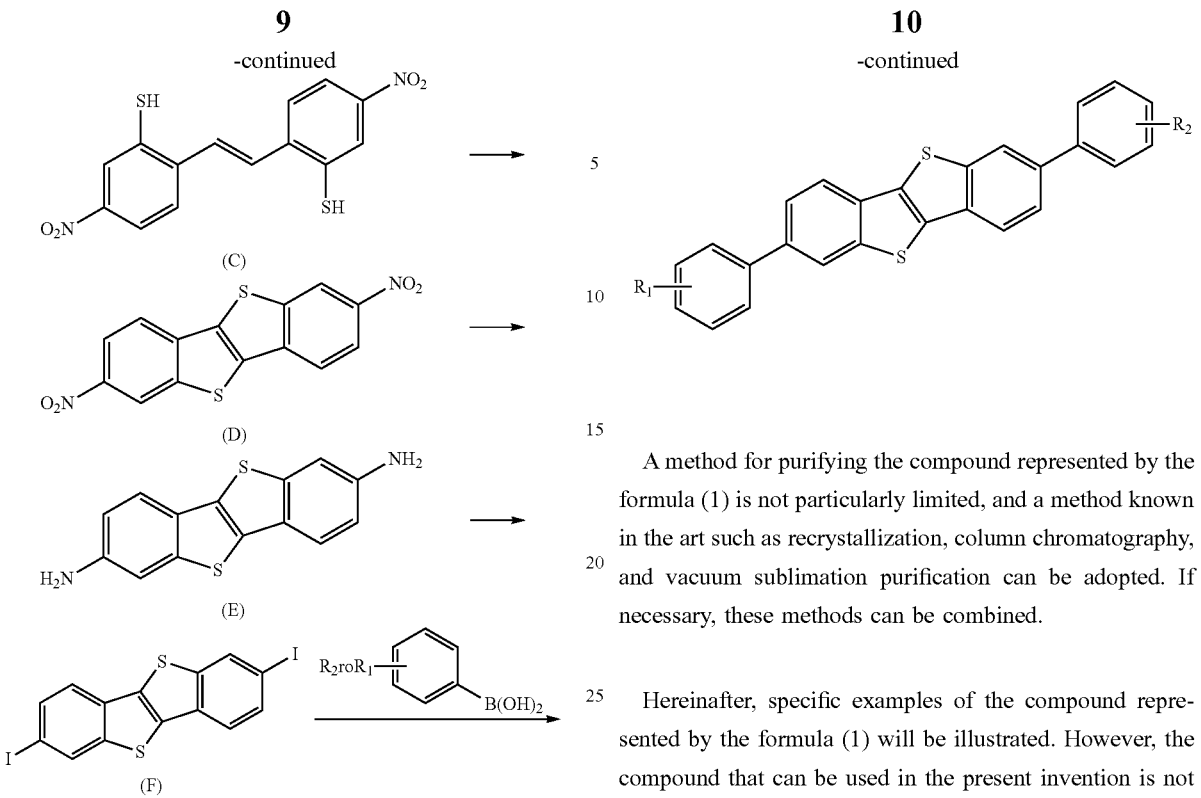

A method for purifying the compound represented by the formula (1) is not particularly limited, and a method known in the art such as recrystallization, column chromatography, and vacuum sublimation purification can be adopted. If necessary, these methods can be combined.

Hereinafter, specific examples of the compound represented by the formula (1) will be illustrated. However, the compound that can be used in the present invention is not limited to these specific examples.

[Formula 6]

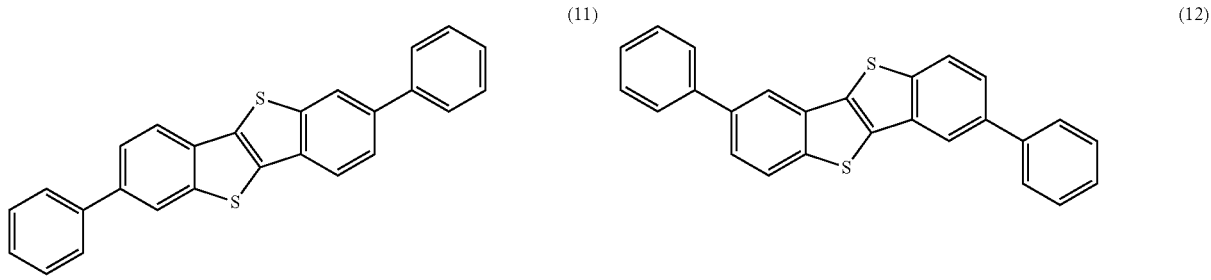

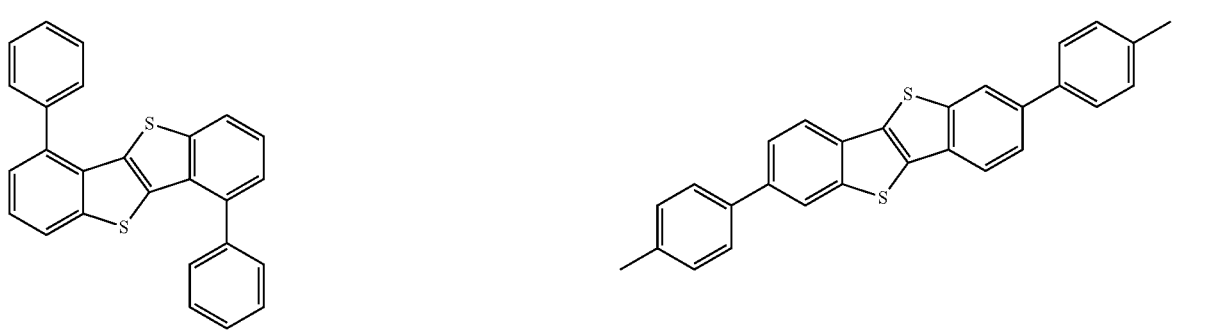

-continued
(15)
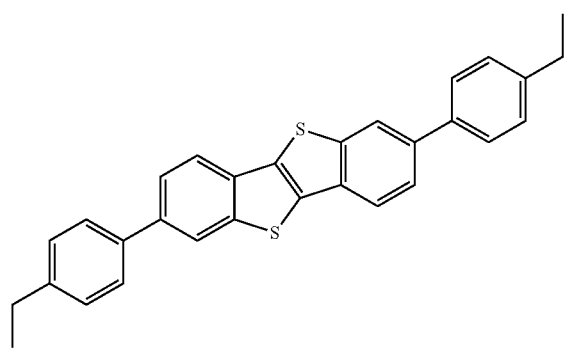
(16)
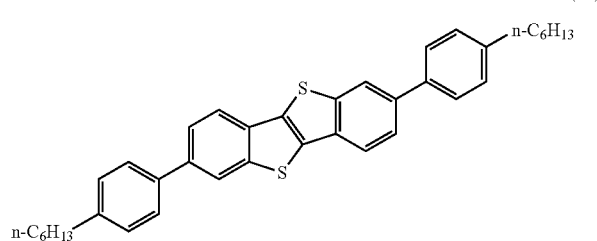
(17)
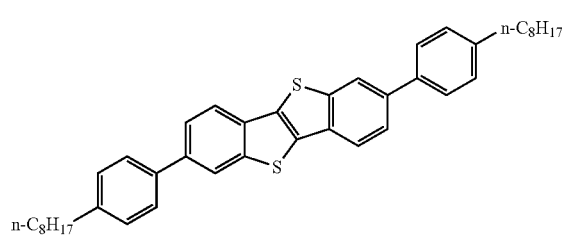
(18)
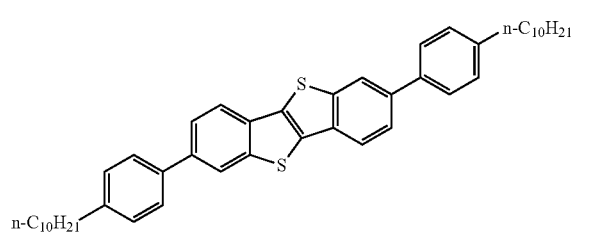
(19)
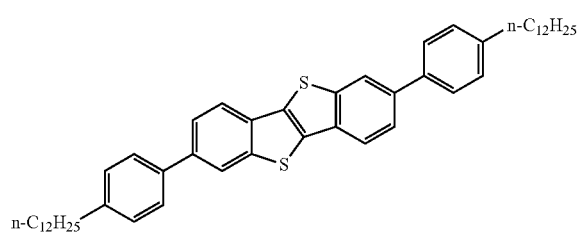
(20)
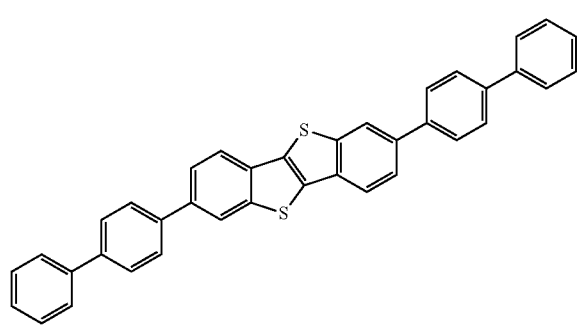
(21)
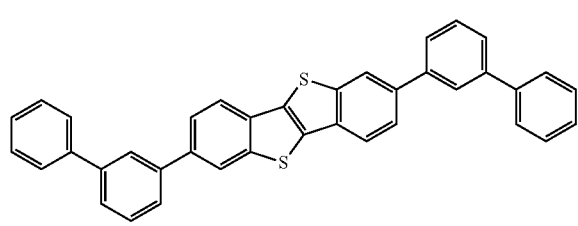
(22)
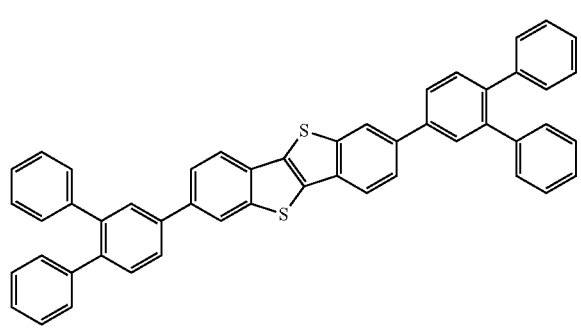

-continued
(23)
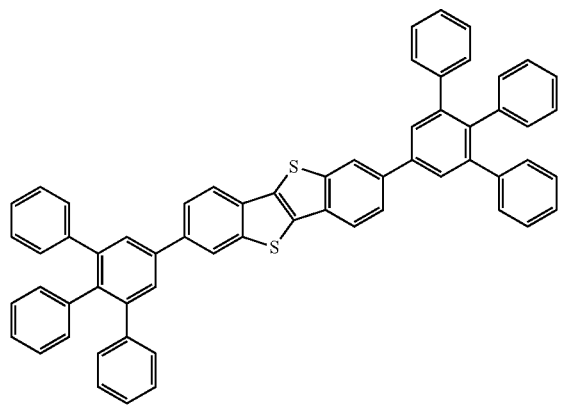
(24)
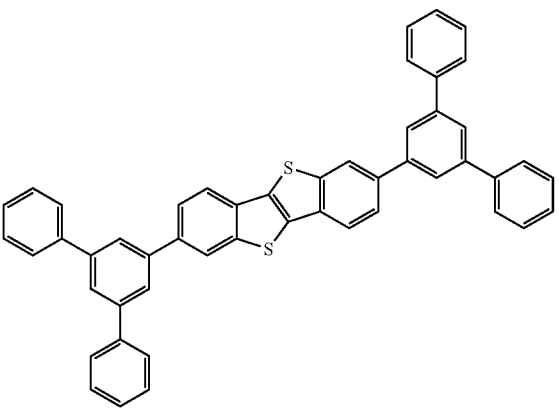
(25)
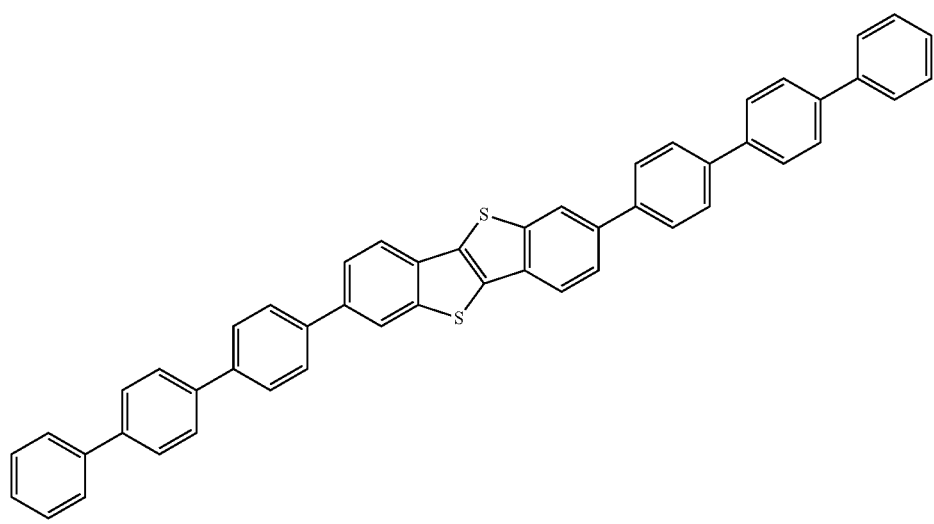
[Formula 7]
(26)
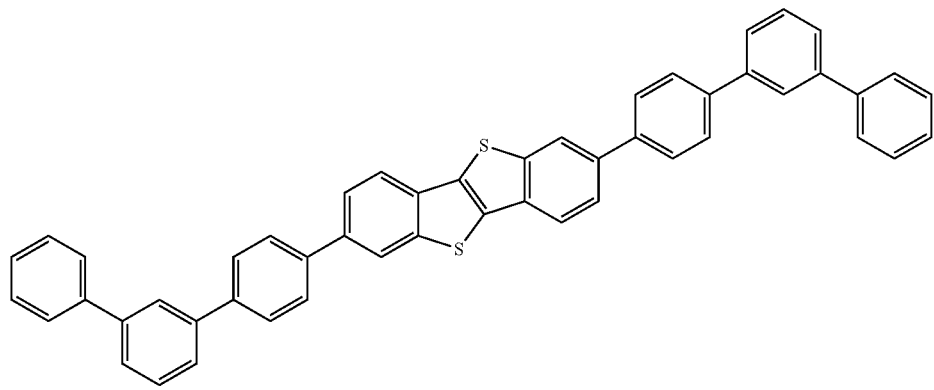

-continued
(27)
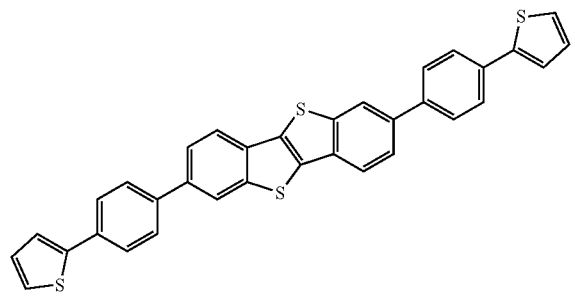
(28)
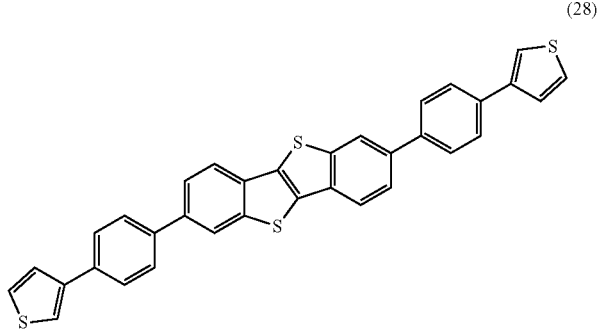
(29)
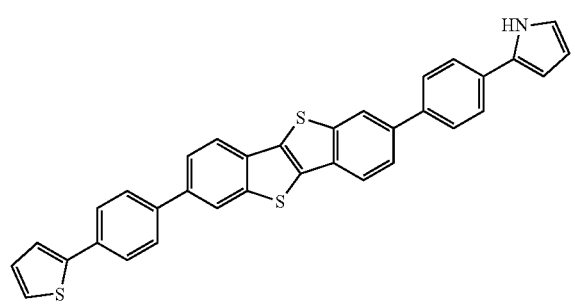
(30)
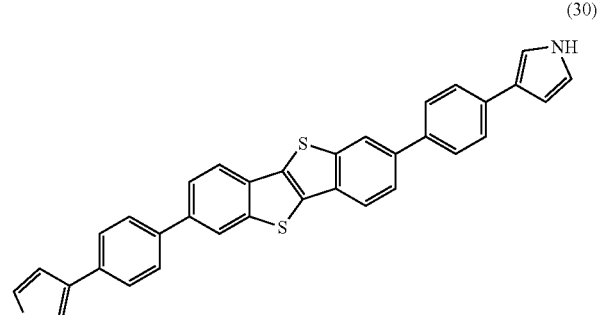
(31)
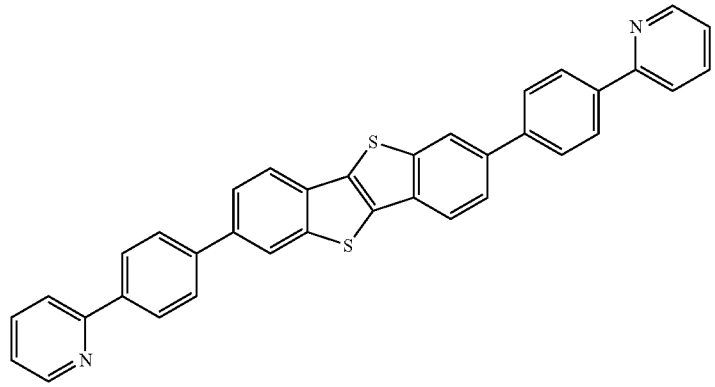
(32)
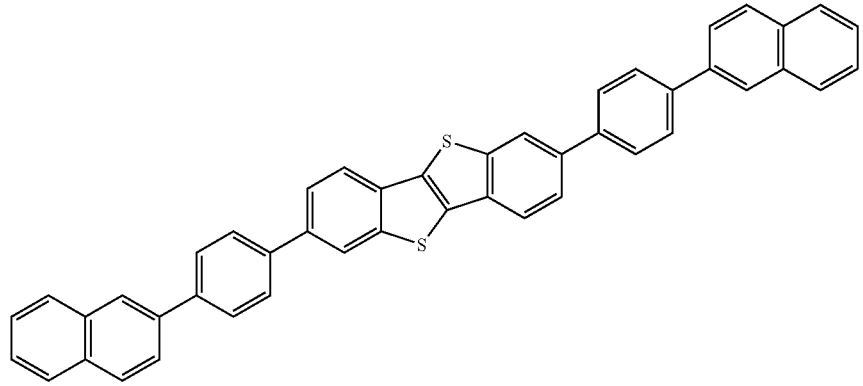

-continued
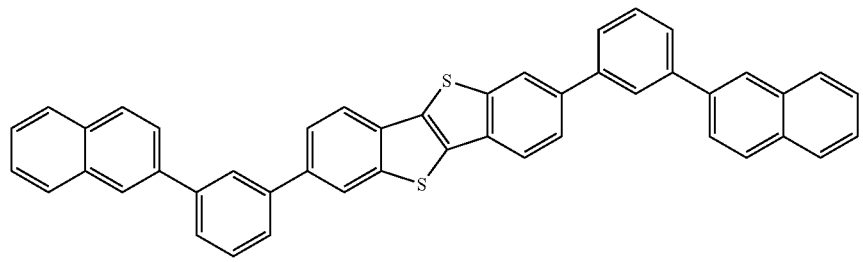
(33)
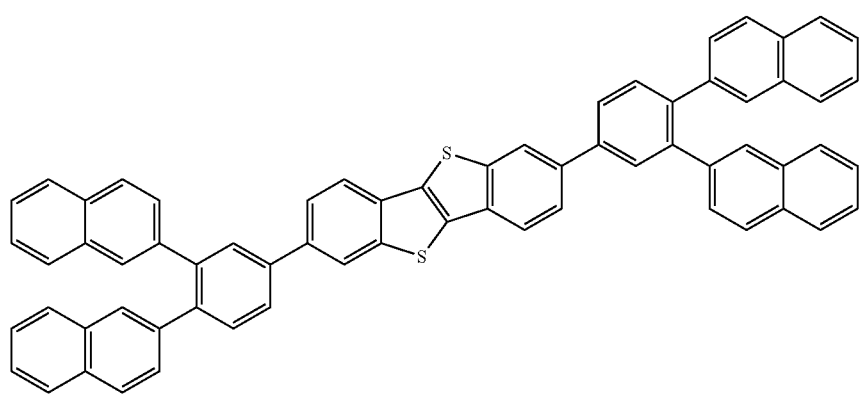
(34)
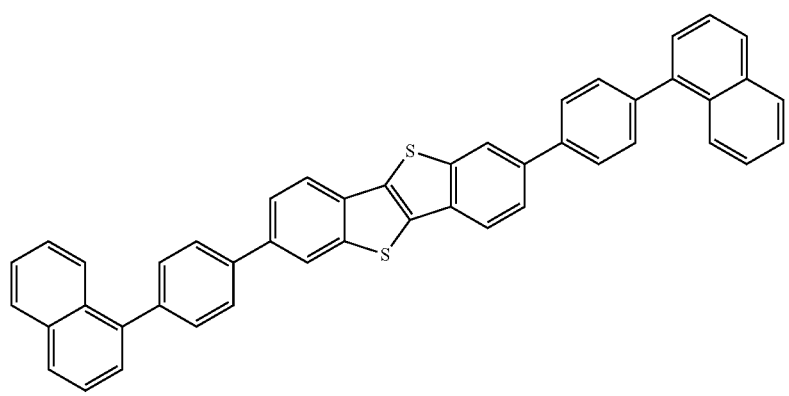
(35)
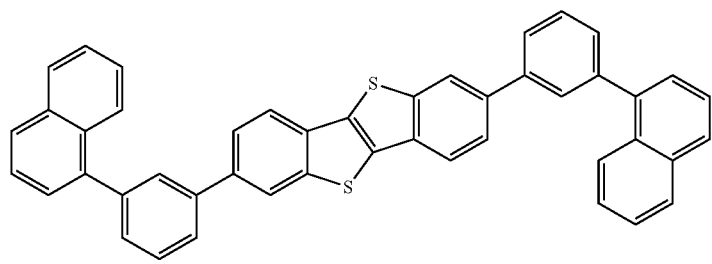
(36)

(37)
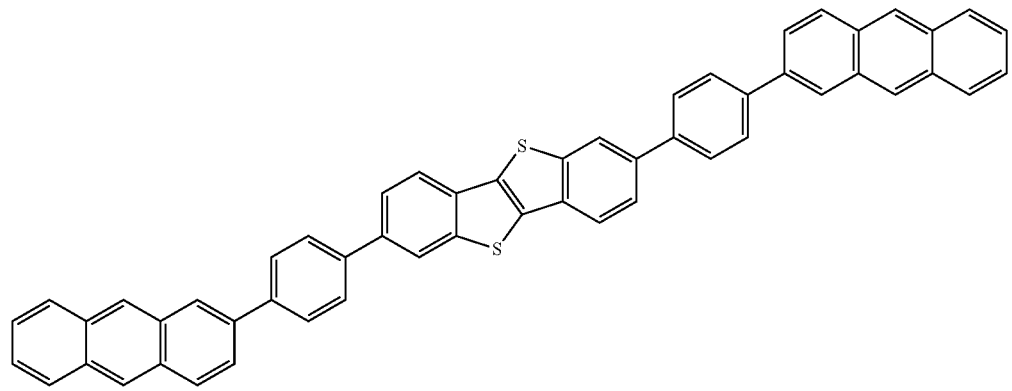
(38)
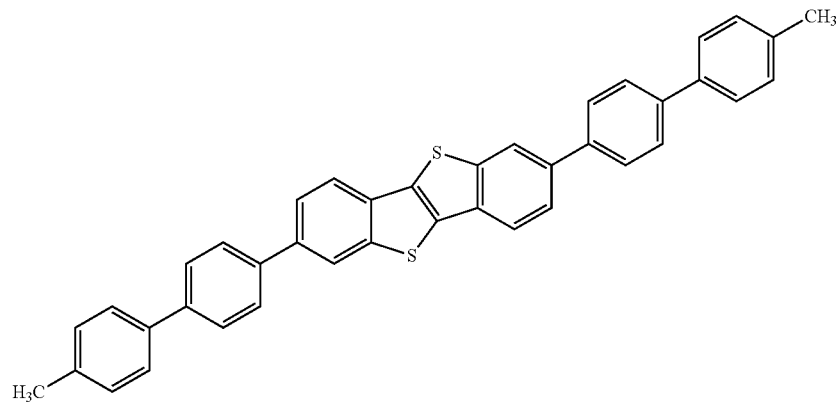
[Formula 8]
(39)
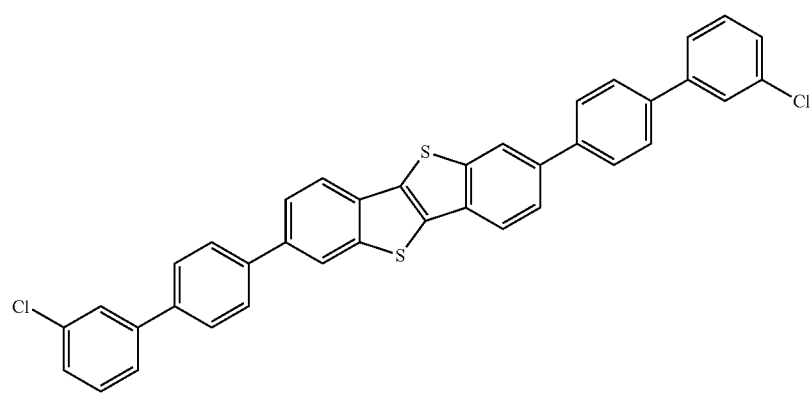

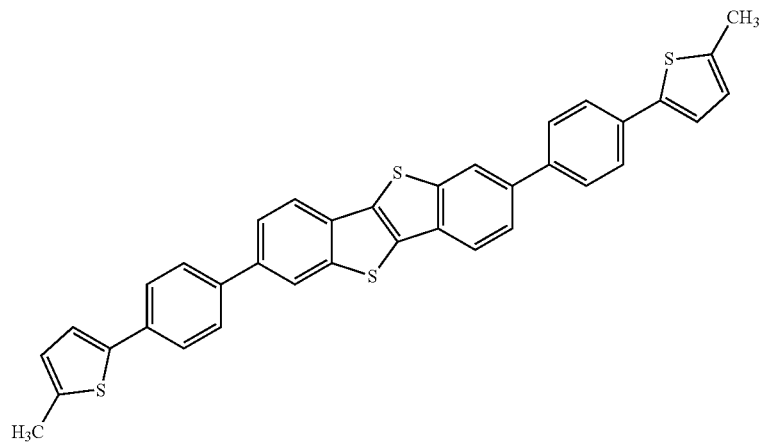
(40)
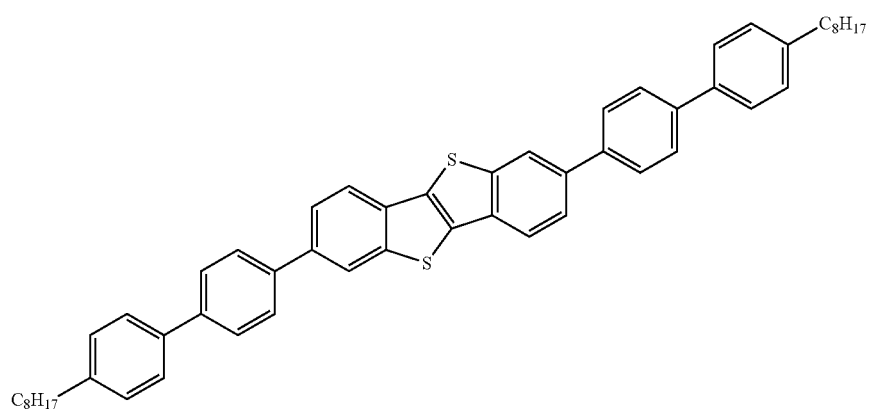
(41)
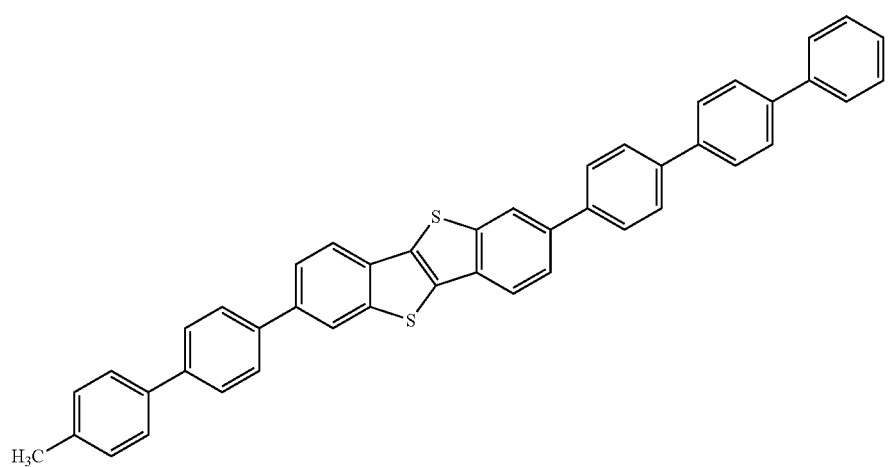
(42)

(43)
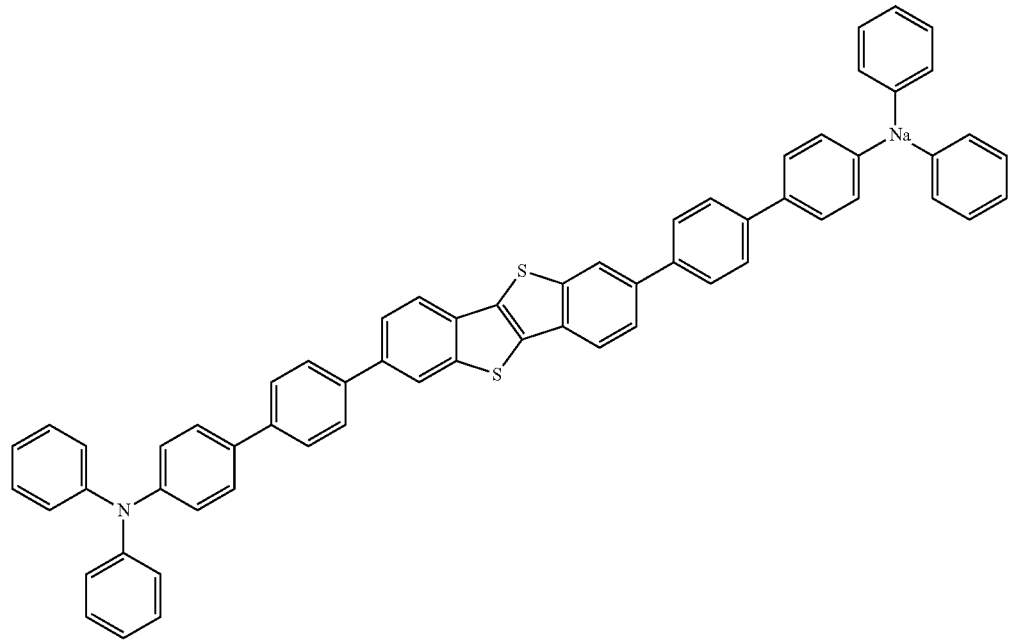
(44)
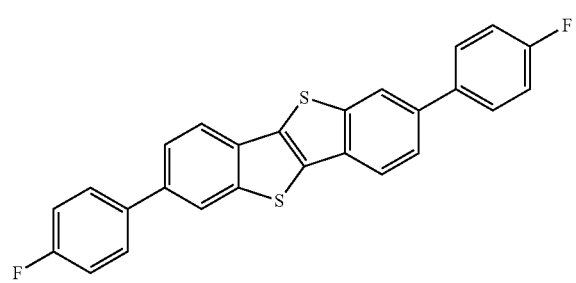
(45)
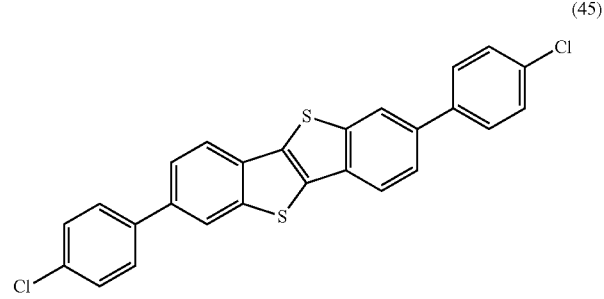
(46)
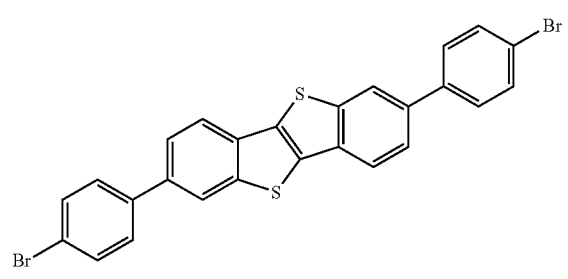
(47)
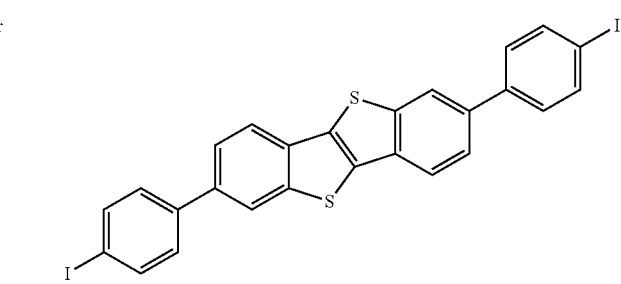
(48)
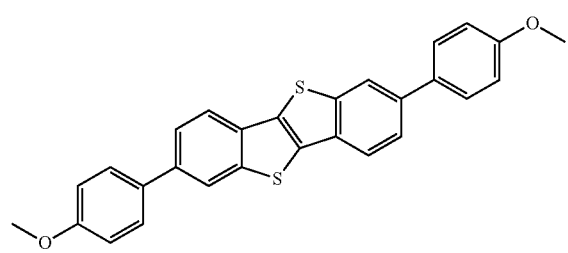
(49)
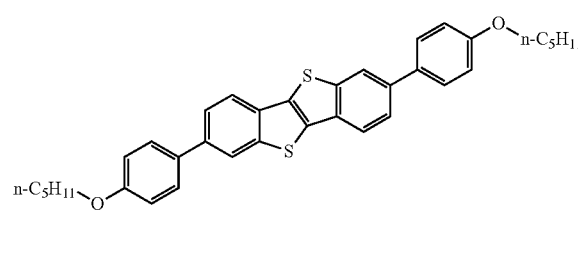

-continued
(50)
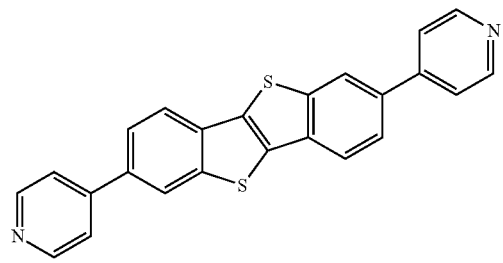
(51)
(52)
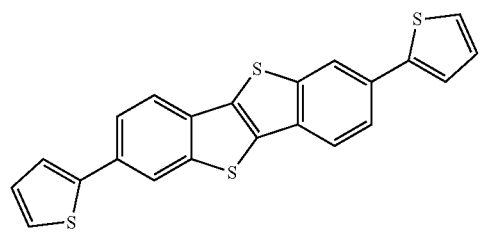
(53)
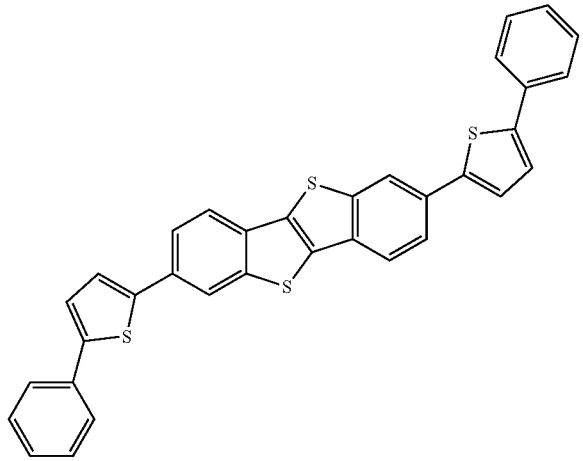
[Formula 9]
(54)
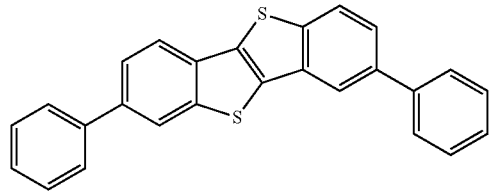
(55)
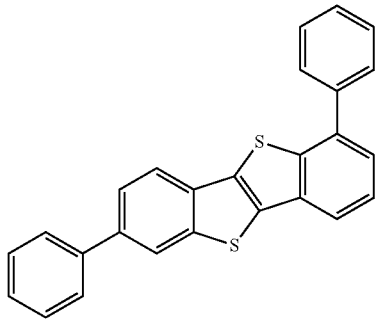
(56)
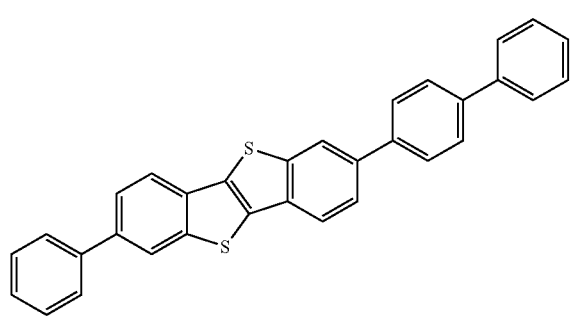
(57)
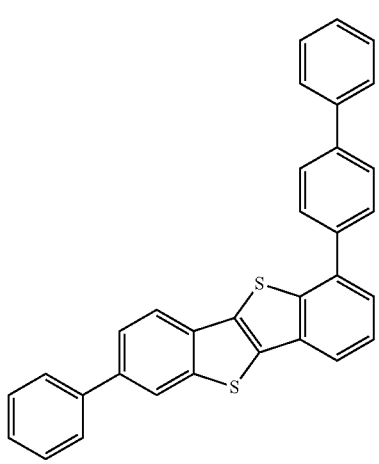

-continued
(58)
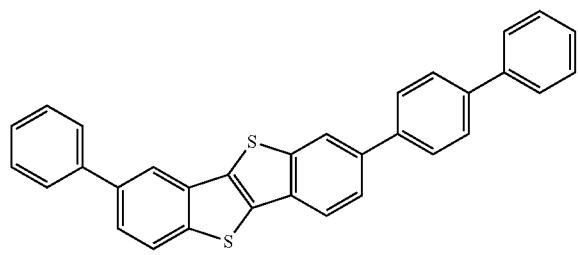
(59)
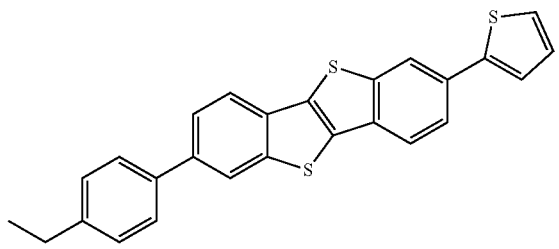
(60)
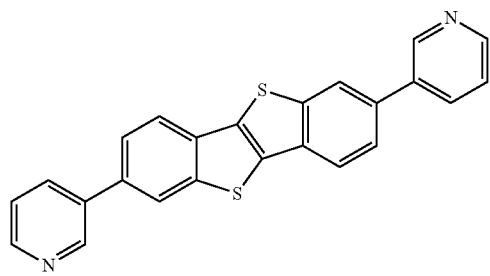
(61)
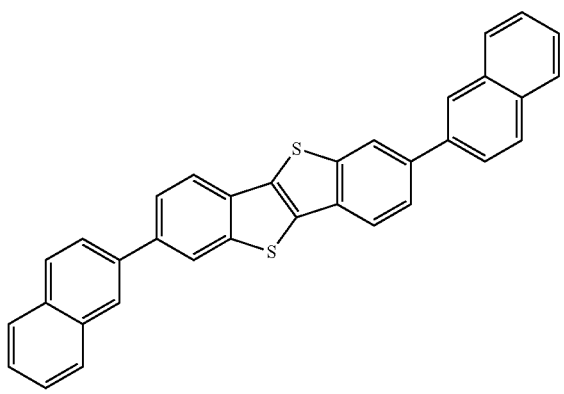
(62)
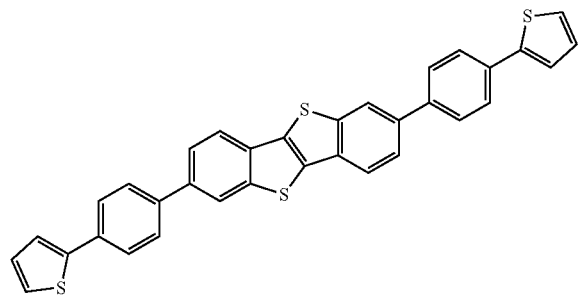
(63)
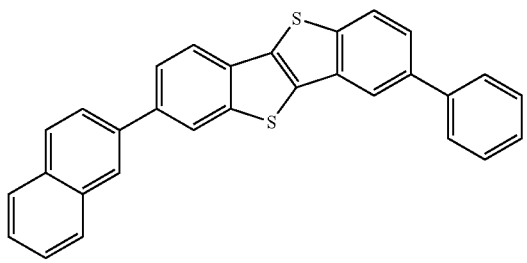
(64)
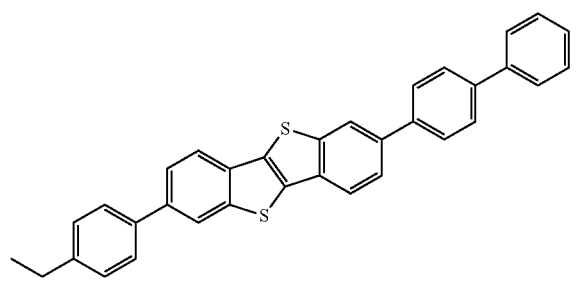
(65)
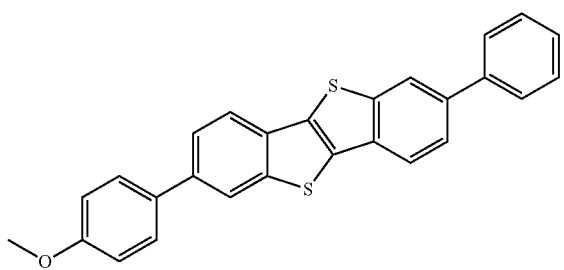
(66)
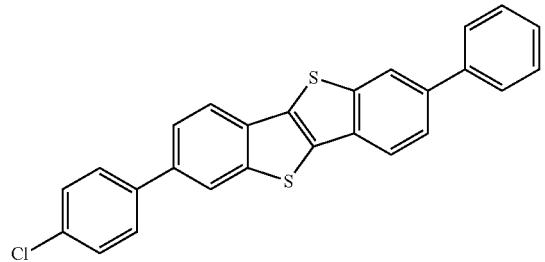
(67)
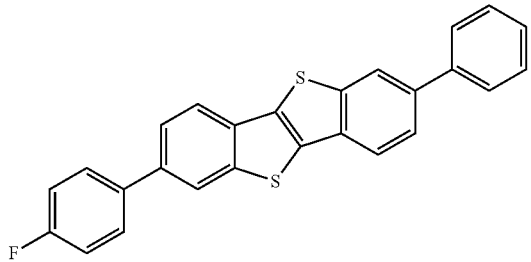

-continued
(68)
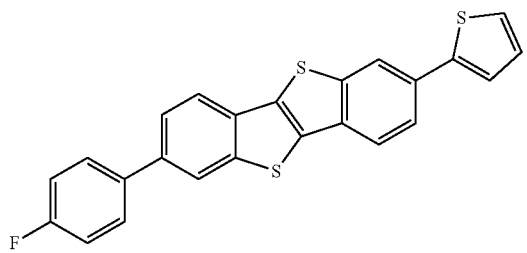
(69)
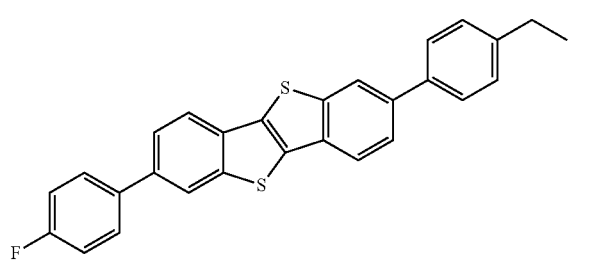
(70)
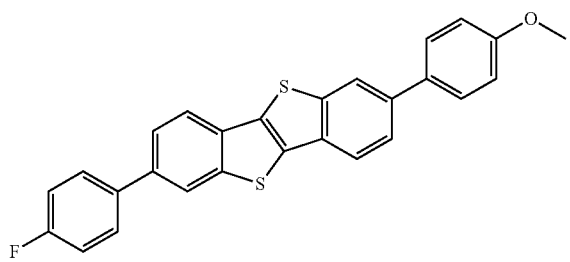
(71)
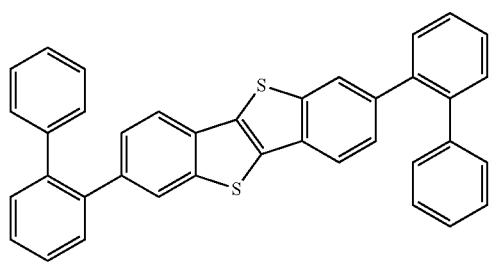
(72)
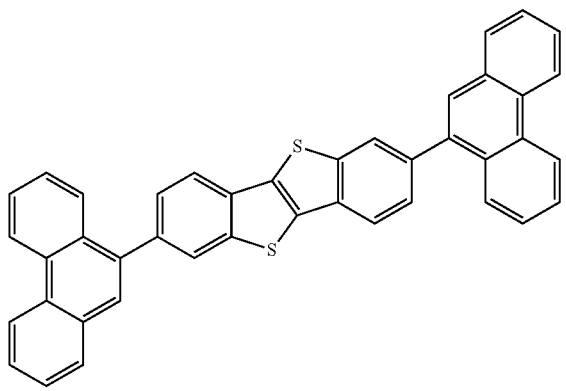
(73)
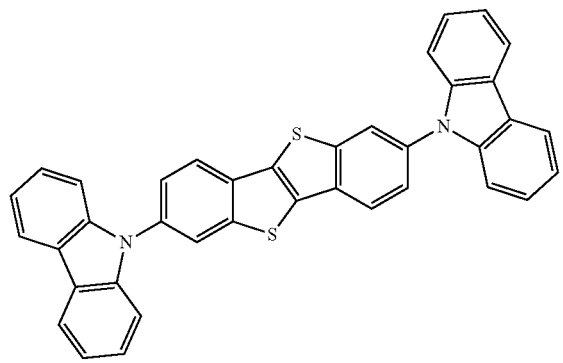
(74)
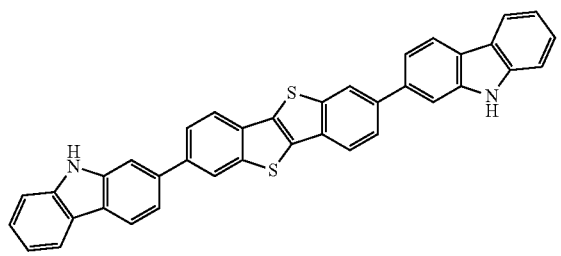
(75)
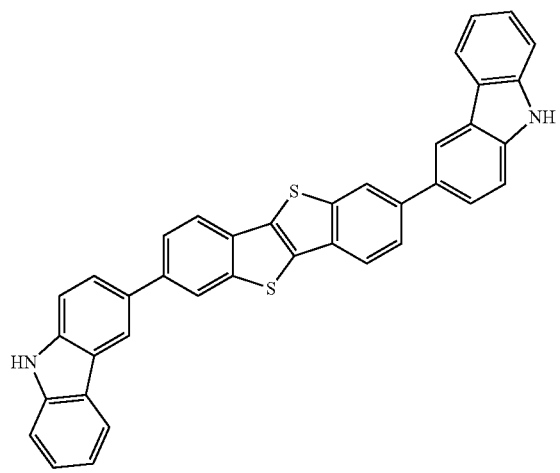

(76)

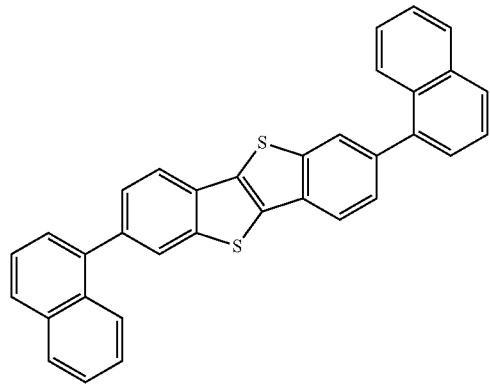

The photoelectric conversion element for use in an imaging element (hereinafter, also simply referred to as the "photoelectric conversion element") of the present invention is an element in which a photoelectric conversion portion (C) is disposed between two electrode films facing each other, i.e., a first electrode film (A) and a second electrode film (B). Light enters the photoelectric conversion portion from above the first electrode film (A) or the second electrode film (B). The photoelectric conversion portion (C) generates electrons and holes according to the intensity of the incident light. A semiconductor reads a signal responding to the charge, and the element exhibits the incident light intensity responding to the absorption wavelength of the photoelectric conversion portion. A transistor for readout may be connected to the electrode film on the side where light does not enter. When a large number of photoelectric conversion elements are arranged in an array pattern, these elements serve as an imaging element because exhibiting the incident light intensity as well as information on the position of incidence. A plurality of photoelectric conversion elements may be laminated for use as long as a photoelectric conversion element positioned closer to a light source does not block (or transmits) the absorption wavelength of a photoelectric conversion element disposed therebehind when viewed from the light source side. A multicolor imaging element (full-color photodiode array) can be formed by laminating and using a plurality of photoelectric conversion elements having their distinctive absorption wavelengths in the visible light region.

The material for a photoelectric conversion element for use in an imaging element of the present invention is used as a material constituting the photoelectric conversion portion (C).

The photoelectric conversion portion (C) is often composed of (c-1) a photoelectric conversion layer and (c-2) one or more organic thin-film layer(s) other than the photoelectric conversion layer, selected from the group consisting of an electron transport layer, a hole transport layer, an electron blocking layer, a hole blocking layer, a crystallization prevention layer, and an interlayer contact improvement layer, etc. The material for a photoelectric conversion element for use in an imaging element of the present invention can be used in any of the photoelectric conversion layer (c-1) and the organic thin-film layer (c-2) other than the photoelectric conversion layer and is preferably used in the organic thin-film layer (c-2) other than the photoelectric conversion layer.

When the photoelectric conversion layer (c-1) comprised in the photoelectric conversion portion (C) mentioned later has hole transport properties or when the organic thin-film layer (c-2) other than the photoelectric conversion layer (hereinafter, the organic thin-film layer other than the photoelectric conversion layer is also simply referred to as the "organic thin-film layer (c-2)") is a hole transport layer having hole transport properties, the first electrode film (A) and the second electrode film (B) carried by the photoelectric conversion element for use in an imaging element of the present invention plays roles in extracting holes from the photoelectric conversion layer (c-1) or the organic thin-film layer (c-2) and collecting the holes. When the photoelectric conversion layer (c-1) comprised in the photoelectric conversion portion (C) has electron transport properties or when the organic thin-film layer (c-2) is an electron transport layer having electron transport properties, the first electrode film (A) and the second electrode film (B) plays roles in extracting electrons from the photoelectric conversion layer (c-1) or the organic thin-film layer (c-2) and discharging the electrons. Accordingly, the material that may be used for each of the first electrode film (A) and the second electrode film (B) is not particularly limited as long as the material has conductivity to some extent. The material is preferably selected in consideration of adhesion to the adjacent photoelectric conversion layer (c-1) or organic thin-film layer (c-2), electron affinity, ionization potential, stability, etc. Examples of the material that may be used for each of the first electrode film (A) and the second electrode film (B) include: conductive metal oxides such as tin oxide (NESA), indium oxide, tin-doped indium oxide (ITO), and zinc-doped indium oxide (IZO); metals such as gold, silver, platinum, chromium, aluminum, iron, cobalt, nickel, and tungsten; inorganic conductive substances such as copper iodide and copper sulfide; conductive polymers such as polythiophene, polypyrrole, and polyaniline; and carbon. These materials may be used, if necessary, as a mixture of two or more thereof or as a laminate of two or more layers thereof. The conductivity of the material for use in each of the first electrode film (A) and the second electrode film (B) is not particularly limited unless the conductivity interferes more than necessary with the light reception of the photoelectric conversion element. The conductivity is preferably as high as possible from the viewpoint of the signal intensity and power consumption of the photoelectric conversion element. For example, an ITO film having conductivity with a sheet resistance of 300Ω/☐ or smaller functions adequately as each of the first electrode film (A) and the second electrode film (B). A commercially available substrate equipped with an ITO film having conductivity with a sheet resistance on the order of several $\Omega/\square$ can also be obtained. Therefore, it is desirable to use such a substrate having high conductivity. The thickness of the ITO film (electrode film) can be arbitrarily selected in consideration of conductivity and is on the order of usually 5 to 500 nm, preferably 10 to 300 nm. Examples of methods for forming the film such as ITO include vapor deposition methods, electron beam methods, sputtering methods, chemical reaction methods, and coating methods conventionally known in the art. The ITO film disposed on the substrate may be provided, if necessary, with UV-ozone treatment, plasma treatment, or the like.

Examples of the material for the transparent electrode film that is used as at least any one (electrode film on the side where light enters) of the first electrode film (A) and the second electrode film (B) include ITO, IZO, $SnO_2$, ATO (antimony-doped tin oxide), ZnO, AZO (Al-doped zinc oxide), GZO (gallium-doped zinc oxide), $TiO_2$, and FTO (fluorine-doped tin oxide). The transmittance of the incident light via the transparent electrode film is preferably 60% or higher, more preferably 80% or higher, particularly preferably 95% or higher, at the absorption peak wavelength of the photoelectric conversion layer (c-1).

In the case of laminating a plurality of photoelectric conversion layers differing in wavelength to be detected, an electrode film (which is an electrode film other than the first electrode film (A) and the second electrode film (B)) for use between the photoelectric conversion layers needs to transmit light having a wavelength other than the light to be detected by each photoelectric conversion layer. For this electrode film, it is preferred to use a material that transmits 90% or more of the incident light, and it is more preferred to use a material that transmits 95% or more of the light.

The electrode films are preferably prepared in a plasma-free form. These electrode films prepared in a plasma-free form can reduce the influence of plasma on the substrate provided with the electrode films and improve the photoelectric conversion characteristics of the photoelectric conversion element. In this context, the term "plasma-free" means that during the film formation of the electrode films, no plasma is generated or the distance from a plasma source to the substrate is 2 cm or more, preferably 10 cm or more, more preferably 20 cm or more, such that the plasma arriving at the substrate is decreased.

Examples of apparatuses that generate no plasma during the film formation of the electrode films include electron beam vapor deposition apparatuses (EB vapor deposition apparatuses) and pulse laser vapor deposition apparatuses. Hereinafter, a film formation method for a transparent electrode film using an EB vapor deposition apparatus is referred to as an EB vapor deposition method, and a film formation method for a transparent electrode film using a pulse laser vapor deposition apparatus is referred to as a pulse laser vapor deposition method.

For example, a facing target sputtering apparatus or an arc plasma vapor deposition apparatus is possible as an apparatus that can achieve a state where plasma can be decreased during the film formation (hereinafter, referred to as a plasma-free film formation apparatus).

In the case of using a transparent conductive film as an electrode film (e.g., a first conductive film), DC short or increase in leakage current may occur. A possible cause thereof is that fine cracks generated in the photoelectric conversion layer are covered with a compact film such as TCO (transparent conductive oxide) to increase continuity with an electrode film (second conductive film) on a side opposite to the transparent conductive film. Therefore, in the case of using a material, such as Al, which has relatively poor film quality in an electrode, increase in leakage current is less likely to occur. The increase in leakage current can be suppressed by controlling the film thickness of each electrode film according to the film thickness (depth of cracks) of the photoelectric conversion layer.

In general, as the conductive film is thinner than the predetermined value, rapid increase in resistance occurs. The sheet resistance of the conductive film in the photoelectric conversion element for use in an imaging element according to the present embodiment is usually 100 to $10000\Omega/\square$ at which the degree of freedom of the film thickness is large. A thinner transparent conductive film absorbs a smaller amount of light and generally has a higher light transmittance. Such a higher light transmittance is very preferred because the light absorbed by the photoelectric conversion layer is increased to improve the photoelectric conversion ability.

The photoelectric conversion portion (C) carried by the photoelectric conversion element for use in an imaging element of the present invention comprises at least (c-1) a photoelectric conversion layer and (c-2) an organic thin-film layer other than the photoelectric conversion layer.

In general, an organic semiconductor film is used as the photoelectric conversion layer (c-1) constituting the photoelectric conversion portion (C). The organic semiconductor film may be one layer or a plurality of layers. For one layer, a P-type organic semiconductor film, an N-type organic semiconductor film, or a mixed film thereof (bulk heterostructure) is used. On the other hand, the plurality of layers are on the order of 2 to 10 layers and have a structure having a laminate of P-type organic semiconductor films, N-type organic semiconductor films, or mixed films thereof (bulk heterostructure). A buffer layer may be inserted between the layers.

A triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a carbazole derivative, a naphthalene derivative, an anthracene derivative, a chrysene derivative, a phenanthrene derivative, a pentacene derivative, a phenylbutadiene derivative, a styryl derivative, a quinoline derivative, a tetracene derivative, a pyrene derivative, a perylene derivative, a fluoranthene derivative, a quinacridone derivative, a coumarin derivative, a porphyrin derivative, a fullerene derivative, a metal complex (Ir complex, Pt complex, Eu complex, etc.), or the like can be used in the organic semiconductor film of the photoelectric conversion layer (c-1) according to the wavelength band to be absorbed.

In the photoelectric conversion element for use in an imaging element of the present invention, the organic thin-film layer (c-2) other than the photoelectric conversion layer constituting the photoelectric conversion portion (C) is also used as a layer other than the photoelectric conversion layer (c-1), for example, an electron transport layer, a hole transport layer, an electron blocking layer, a hole blocking layer, a crystallization prevention layer, or an interlayer contact improvement layer. Particularly, it is preferred to use the organic thin-film layer (c-2) as one or more thin-film layer(s) selected from the group consisting of an electron transport layer, a hole transport layer, an electron blocking layer, and a hole blocking layer, because the resulting element efficiently converts even weak light energy to an electric signal.

The electron transport layer plays roles in transporting electrons generated in the photoelectric conversion layer (c-1) to the first electrode film (A) or the second electrode film (B) and blocking the transfer of holes from the electrode film as an electron acceptor to the photoelectric conversion layer (c-1).

The hole transport layer plays roles in transporting generated holes from the photoelectric conversion layer (c-1) to the first electrode film (A) or the second electrode film (B) and blocking the transfer of electrons from the electrode film as a hole acceptor to the photoelectric conversion layer (c-1).

The electron blocking layer plays roles in blocking the transfer of electrons from the first electrode film (A) or the second electrode film (B) to the photoelectric conversion layer (c-1), preventing recombination in the photoelectric conversion layer (c-1), and reducing dark current.

The hole blocking layer has the functions of blocking the transfer of holes from the first electrode film (A) or the second electrode film (B) to the photoelectric conversion layer (c-1), preventing recombination in the photoelectric conversion layer (c-1), and reducing dark current.

The hole blocking layer is formed by using alone a substance capable of blocking holes or by mixing and laminating two or more of substances capable of blocking holes. The substance capable of blocking holes is not limited as long as the substance is a compound that can prevent the efflux of the holes from the electrode to the outside of the element. Examples of the compound that can be used in the hole blocking layer include the compound represented by the general formula (1) as well as phenanthroline derivatives such as bathophenanthroline and bathocuproine, silole derivatives, quinolinol derivative-metal complexes, oxadiazole derivatives, oxazole derivatives, and quinoline derivatives. One or two or more of these compounds can be used.

The organic thin-film layer (c-2) other than the photoelectric conversion layer, comprising the compound represented by the general formula (1) can be suitably used, particularly, as a hole blocking layer. A larger film thickness of the hole blocking layer is more preferred from the viewpoint of preventing leakage current. A film thickness as small as possible is more preferred from the viewpoint of obtaining a sufficient amount of current for signal readout at the time of light incidence. For achieving these conflicting characteristics, it is generally preferred that the photoelectric conversion portion (C) comprising the layers (c-1) and (c-2) should have a film thickness on the order of 5 to 500 nm. How the layer comprising the compound represented by the general formula (1) works varies depending on the other compounds used in the photoelectric conversion element.

For avoiding interference with the light absorption of the photoelectric conversion layer (c-1), it is preferred that the hole blocking layer and the electron blocking layer should have a high transmittance at the absorption wavelength of the photoelectric conversion layer and should be used as thin films.

FIG. 1 illustrates the details of a typical element structure of the photoelectric conversion element for use in an imaging element of the present invention. However, the present invention is not intended to be limited by this structure. In the exemplary embodiment of FIG. 1, 1 denotes an insulation portion, 2 denotes one of the electrode films (first electrode film or second electrode film), 3 denotes an electron blocking layer, 4 denotes a photoelectric conversion layer, 5 denotes a hole blocking layer, 6 denotes the other electrode film (second electrode film or first electrode film), and 7 denotes an insulating base material or a laminated photoelectric conversion element. A readout transistor (not shown in the drawing) can be connected to either of the electrode film 2 or 6. For example, provided that the photoelectric conversion layer 4 is transparent, this film may be formed on the outside of the electrode film on a side opposite to the side where light enters (i.e., the upside of the electrode film 2 or the downside of the electrode film 6). Provided that a thin-film layer (electron blocking layer, hole blocking layer, etc.) other than the photoelectric conversion layer constituting the photoelectric conversion element dose not extremely mask the absorption wavelength of the photoelectric conversion layer, the incident direction of light can be any of the downward direction (incidence from the insulation portion 1 side in FIG. 1) or the upward direction (incidence from the insulating base material 7 side in FIG. 1).

In general, for example, a vacuum process (resistance heating vacuum vapor deposition, electron beam vapor deposition, sputtering, and molecular lamination), a solution process (coating methods such as casting, spin coating, dip coating, blade coating, wire bar coating, and spray coating; printing methods such as inkjet printing, screen printing, offset printing, and relief printing; and soft lithography approaches such as microcontact printing), or a method using a combination of two or more of these approaches can be adopted as a method for forming the photoelectric conversion layer (c-1) and the organic thin-film layer (c-2) other than the photoelectric conversion layer in the photoelectric conversion element for use in an imaging element of the present invention. The thickness of each layer also depends on the resistance and charge mobility of each substance and thus, cannot be limited. The thickness of each layer is usually in the range of 0.5 to 5000 nm, preferably in the range of 1 to 1000 nm, more preferably in the range of 5 to 500 nm.

EXAMPLES

Hereinafter, the present invention will be described in more detail with reference to Examples. However, the present invention is not intended to be limited by these examples.

The blocking layer described in Examples can be any of the hole blocking layer and the electron blocking layer. In Examples 1 to 3 and Comparative Example 1, the photoelectric conversion element was prepared in a vapor deposition machine, and the application and measurement of current and voltage were conducted in the atmosphere. In Examples 4 to 8, the photoelectric conversion element was prepared in a vapor deposition machine integrated with a glove box, and the prepared photoelectric conversion element was placed in a hermetically sealable bottle-shaped measurement chamber (manufactured by ALS Technology Co., Ltd.) in the glove box having a nitrogen atmosphere, and subjected to the application and measurement of current and voltage. The application and measurement of current and voltage were conducted using a semiconductor parameter analyzer 4200-SCS (Keithley Instruments, Inc.), unless otherwise specified. Irradiation with incident light was carried out at a light wavelength of 550 nm and a light half-value width of 20 nm using PVL-3300 (manufactured by Asahi Spectra Co., Ltd.), unless otherwise specified. In Examples, a light-dark ratio represents a value determined by dividing a current value in the case of light irradiation by a current value in the dark.

Example 1 Preparation of Photoelectric Conversion Element and Evaluation Thereof On ITO transparent conductive glass (manufactured by GEOMATEC Co., Ltd., ITO film thickness: 150 nm), a film of 2,7-diphenyl[1]benzothieno[3,2-b][1]benzothiophene (compound represented by the formula (11) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied using the ITO and aluminum electrodes, the current in the dark was $-1.68 \times 10^{-10}$ A/cm$^2$. When a voltage of 5 V was applied to the transparent conductive glass side, the current in the case of light irradiation was $-1.01 \times 10^{-7}$ A/cm. When a voltage of 5 V was applied to the transparent conductive glass side, the light-dark ratio was 600.

Example 2 Preparation of Photoelectric Conversion Element and Evaluation Thereof On ITO transparent conductive glass (manufactured by GEOMATEC Co., Ltd., ITO film thickness: 150 nm), a film of 2,7-bis(4-methylphenyl) [1]benzothieno[3,2-b][1]benzothiophene (compound represented by the formula (14) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied using the ITO and aluminum electrodes, the current in the dark was $-8.85 \times 10^{-11}$ A/cm$^2$. When a voltage of 5 V was applied to the transparent conductive glass side, the current in the case of light irradiation was $-3.05 \times 10^{-7}$ A/cm$^2$. When a voltage of 5 V was applied to the transparent conductive glass side, the light-dark ratio was 3500.

Example 3 Preparation of Photoelectric Conversion Element and Evaluation Thereof On ITO transparent conductive glass (manufactured by GEOMATEC Co., Ltd., ITO film thickness: 150 nm), a film of 2,7-bis(4-ethylphenyl) [1]benzothieno[3,2-b][1]benzothiophene (compound represented by the formula (15 in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied using the ITO and aluminum electrodes, the current in the dark was $1.41 \times 10^{-10}$ A/cm$^2$. When a voltage of 5 V was applied to the transparent conductive glass side, the current in the case of light irradiation was $5.47 \times 10^{-7}$ A/cm$^2$. When a voltage of 5 V was applied to the transparent conductive glass side, the light-dark ratio was 3900.

Comparative Example 1 Preparation of Photoelectric Conversion Element and Evaluation Thereof On ITO transparent conductive glass (manufactured by GEOMATEC Co., Ltd., ITO film thickness: 150 nm), a film of tris(8-quinolinato)aluminum was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare a photoelectric conversion element for use in an imaging element for comparison. When a voltage of 5 V was applied using the ITO and aluminum electrodes, the current in the dark was $-1.06 \times 10^{-10}$ A/cm$^2$. When a voltage of 5 V was applied to the transparent conductive glass side, the current in the case of light irradiation was $-3.33 \times 10^{-9}$ A/cm$^2$. When a voltage of 5 V was applied to the transparent conductive glass side, the light-dark ratio was 31.

The dark current-voltage graph obtained in the evaluation of Examples 1 to 3 and Comparative Example 1 described above is shown in FIG. 2, and the light current-voltage graph obtained therein is shown in FIG. 3. As is evident from FIGS. 2 and 3 and the Examples described above, the photoelectric conversion element for use in an imaging element of the present invention exhibits dark current prevention properties equivalent to the photoelectric conversion element for use in an imaging element for comparison, and is superior in light current characteristics to the photoelectric conversion element for use in an imaging element for comparison.

Example 4 Preparation of Photoelectric Conversion Element and Evaluation Thereof On ITO transparent conductive glass (manufactured by GEOMATEC Co., Ltd., ITO film thickness: 150 nm), a film of 2,7-bis(p-biphenyl)-[1]benzothieno[3,2-b][1]benzothiophene (compound represented by the formula (20) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied to the transparent conductive glass side using the ITO and aluminum electrodes, the light-dark ratio was 15000.

Example 5 Preparation of Photoelectric Conversion Element and Evaluation Thereof On ITO transparent conductive glass (manufactured by GEOMATEC Co., Ltd., ITO film thickness: 150 nm), a film of 2,7-bis(m-biphenyl)-[1]benzothieno[3,2-b][1]benzothiophene (compound represented by the formula (21) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied to the transparent conductive glass side using the ITO and aluminum electrodes, the light-dark ratio was 1800.

Example 6 Preparation of Photoelectric Conversion Element and Evaluation Thereof On ITO transparent conductive glass (manufactured by GEOMATEC Co., Ltd., ITO film thickness: 150 nm), a film of 2,7-bis(9-phenanthrenyl)-[1]benzothieno[3,2-b][1]benzothiophene (compound represented by the formula (72) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied to the transparent conductive glass side using the ITO and aluminum electrodes, the light-dark ratio was 690.

Example 7 Preparation of Photoelectric Conversion Element and Evaluation Thereof On ITO transparent conductive glass (manufactured by GEOMATEC Co., Ltd., ITO film thickness: 150 nm), a film of 2,7-bis(l-naphthyl)-[1]benzothieno[3,2-b][1]benzothiophene (compound represented by the formula (76) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied to the transparent conductive glass side using the ITO and aluminum electrodes, the light-dark ratio was 240.

Example 8 Preparation of Photoelectric Conversion Element and Evaluation Thereof On ITO transparent conductive glass (manufactured by GEOMATEC Co., Ltd., ITO film thickness: 150 nm), a film of 2,7-bis(9H-carbazol-9-yl)-[1]benzothieno[3,2-b][1]benzothiophene (compound represented by the formula (73) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied to the transparent conductive glass side using the ITO and aluminum electrodes, the light-dark ratio was 47.

The light-dark ratios obtained in the evaluation of Examples 4 to 8 described above evidently show excellent characteristics as a photoelectric conversion element for use in an imaging element.

Synthesis Example 1 Synthesis of 2-([1,1':4',1"-terphenyl]-4-yl)-4,4,5,5-tetramethyl-1,3,2-dioxabolorane 200 parts of toluene, 5 parts of 4-bromo-1,1':4',1"-terphenyl, 5 parts of bis(pinacolato)diboron, 3 parts of potassium acetate, and 0.5 parts of [1,1'-bis(diphenylphosphino)ferrocene]palladium(II) dichloride dichloromethane adduct were mixed and stirred for 4 hours in a nitrogen atmosphere at a reflux temperature. The obtained solution was cooled to room temperature. Then, 20 parts of silica gel were added thereto, and the mixture was stirred for 5 minutes. Then, solid matter was collected by filtration, and the solvent was distilled off under reduced pressure to obtain 5.5 parts of 2-([1,1':4',1"-terphenyl]-4-yl)-4,4,5,5-tetramethyl-1,3,2-dioxabolorane represented by the following formula (100) as a white solid:

[Formula 10]

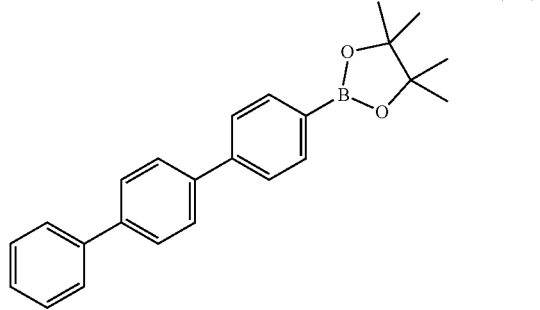

(100)

Synthesis Example 2 Synthesis of 2,7-bis(1,1':4',1"-terphenyl-4-yl)-[1]benzothieno[3,2-b][1]benzothiophene 120 parts of DMF, 3.5 parts of 2-([1,1':4',1"-terphenyl]-4-yl)-4,4,5,5-tetramethyl-1,3,2-dioxabolorane obtained in Synthesis Example 1, 2.1 parts of 2,7-diiodo[1]benzothieno[3,2-b][1]benzothiophene, 14 parts of tripotassium phosphate, 4.0 parts of water, and 0.3 parts of tetrakis(triphenylphosphine)palladium(0) were mixed and stirred for 6 hours in a nitrogen atmosphere at 90° C. The obtained solution was cooled to room temperature. Then, 120 parts of water were added thereto, and solid matter was collected by filtration. The obtained solid was washed with acetone, dried, and then purified by sublimation to obtain 3.0 parts of 2,7-bis(1,1':4',1"-terphenyl-4-yl)-[1]benzothieno[3,2-b][1]benzothiophene (compound represented by the formula (25) in the specific examples described above).

Example 9 Preparation of Photoelectric Conversion Element and Evaluation Thereof On ITO transparent conductive glass (manufactured by GEOMATEC Co., Ltd., ITO film thickness: 150 nm), a film of 2,7-bis(1,1':4',1''-terphenyl-4-yl)-[1]benzothieno[3,2-b][1]benzothiophene (compound represented by the formula (25) in the specific examples described above) was formed as a blocking layer having a thickness of 50 nm by resistance heating vacuum vapor deposition. Next, on the blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied to the transparent conductive glass side using the ITO and aluminum electrodes, the light-dark ratio was 140000.

The light-dark ratio obtained in the evaluation of Example 9 described above evidently shows excellent characteristics as a photoelectric conversion element for use in an imaging element.

INDUSTRIAL APPLICABILITY

As described above, the compound represented by the formula (1) or the formula (2) has performance excellent in organic photoelectric conversion characteristics and is expected to be applied to fields including organic imaging elements having high resolution and high responsiveness as well as devices such as organic solar cells, photosensors, infrared sensors, ultraviolet sensors, X-ray sensors, and photon counters, cameras, video cameras, infrared cameras, etc., using these devices.

REFERENCE SIGNS LIST

1: Insulation portion
2: Upper electrode
3: Electron blocking layer or hole transport layer
4: Photoelectric conversion layer
5: Hole blocking layer or electron transport layer
6: Lower electrode
7: Insulating base material or another photoelectric conversion element

The invention claimed is:

1. An imaging element in which a photoelectric conversion element comprises:
   (A) a first electrode film,
   (B) a second electrode film physically distinct from the first electrode film, and
   (C) a photoelectric conversion portion disposed between the first electrode film and the second electrode film,
   wherein the photoelectric conversion portion (C) comprises at least
      (c-1) a photoelectric conversion layer and
      (c-2) an organic thin-film layer other than the photoelectric conversion layer, and
   wherein the organic thin-film layer (c-2) comprises a material for the photoelectric conversion element comprising a compound represented by formula (2):

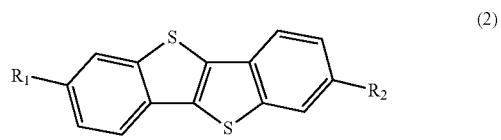

(2)

wherein $R_1$ and $R_2$ each independently represents a substituted or unsubstituted aromatic group, wherein a substitution group of the aromatic group is selected from the group consisting of an alkyl group, an alkoxy group, an aromatic group, a halogen atom, a hydroxyl group, a mercapto group, a nitro group, an alkyl-substituted amino group, an aryl-substituted amino group, an unsubstituted amino group, an acyl group, an alkoxycarbonyl group, a cyano group, and an isocyano group.

2. The imaging element according to claim 1, wherein a plurality of the photoelectric conversion element are arranged in an array pattern.

3. The imaging element according to claim 1, wherein $R_1$ and $R_2$ in formula (2) are each independently a substituted or unsubstituted aromatic hydrocarbon group.

4. The imaging element according to claim 3, wherein each of $R_1$ and $R_2$ in formula (2) is a substituted or unsubstituted phenyl group.

5. The imaging element according to claim 4, wherein each of $R_1$ and $R_2$ in formula (2) is a phenyl group having a substituted or unsubstituted aromatic hydrocarbon group.

6. The imaging element according to claim 5, wherein each of $R_1$ and $R_2$ in formula (2) is a phenyl group having a substituted or unsubstituted phenyl group.

7. The imaging element according to claim 6, wherein each of $R_1$ and $R_2$ in formula (2) is a phenyl group having a biphenyl group.

8. The imaging element according to claim 4, wherein each of $R_1$ and $R_2$ in formula (2) is a phenyl group having an alkyl group having 1 to 12 carbon atoms.

9. The imaging element according to claim 8, wherein each of $R_1$ and $R_2$ in formula (2) is a phenyl group having a methyl group or an ethyl group.

10. The imaging element according to claim 1, wherein the organic thin-film layer (c-2) other than the photoelectric conversion layer is an electron blocking layer.

11. The imaging element according to claim 1, wherein the organic thin-film layer (c-2) other than the photoelectric conversion layer is a hole blocking layer.

12. The imaging element according to claim 1, wherein the organic thin-film layer (c-2) other than the photoelectric conversion layer is an electron transport layer.

13. The imaging element according to claim 1, wherein the organic thin-film layer (c-2) other than the photoelectric conversion layer is a hole transport layer.

14. An imaging element in which a photoelectric conversion element comprises:
   (A) a first electrode film,
   (B) a second electrode film physically distinct from the first electrode film, and
   (C) a photoelectric conversion portion disposed between the first electrode film and the second electrode film,
   wherein the photoelectric conversion portion (C) comprises at least (c-1) a photoelectric conversion layer and (c-2) an organic thin-film layer other than the photoelectric conversion layer, and
   wherein an organic thin-film layer of (c-1) the photoelectric conversion layer comprises a material for the photoelectric conversion element comprising the compound represented by a material for the photoelectric conversion element comprising a compound represented by formula (2):

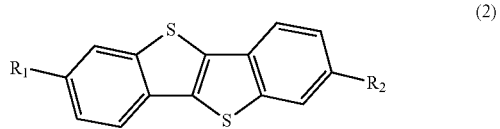

wherein $R_1$ and $R_2$ each independently represents a substituted or unsubstituted aromatic group, wherein a substitution group of the aromatic group is selected from the group consisting of an alkyl group, an alkoxy group, an aromatic group, a halogen atom, a hydroxyl group, a mercapto group, a nitro group, an alkyl-substituted amino group, an aryl-substituted amino group, an unsubstituted amino group, an acyl group, an alkoxycarbonyl group, a cyano group, and an isocyano group.

15. The imaging element according to claim 1, further comprising:

(D) a thin-film transistor having a hole accumulation portion, and (E) a signal readout portion which reads a signal responding to charge accumulated in the thin-film transistor.

16. The imaging element according to claim 15, wherein the thin-film transistor (D) having a hole accumulation portion further comprises (d) a connection portion that electrically connects the hole accumulation portion to any one of the first electrode film and the second electrode film.

17. The imaging element according to claim 14, wherein a plurality of the photoelectric conversion element are arranged in an array pattern.

18. The imaging element according to claim 1, wherein the first electrode film and the second electrode film are made of a same material.

19. The imaging element according to claim 1, wherein a material of the first electrode film is different from a material of the second electrode film.

20. The imaging element according to claim 14, wherein the first electrode film and the second electrode film are made of a same material.

21. The imaging element according to claim 14, wherein a material of the first electrode film is different from a material of the second electrode film.

* * * * *